US007125701B2

(12) United States Patent
Agostino et al.

(10) Patent No.: US 7,125,701 B2
(45) Date of Patent: Oct. 24, 2006

(54) AGGRECANASE MOLECULES

(75) Inventors: Michael J. Agostino, Andover, MA (US); Lisa A. Racie, Acton, MA (US)

(73) Assignee: Wyeth, Madison, NJ (US)

( * ) Notice: Subject to any disclaimer, the term of this patent is extended or adjusted under 35 U.S.C. 154(b) by 519 days.

(21) Appl. No.: 10/205,368

(22) Filed: Jul. 26, 2002

(65) Prior Publication Data

US 2003/0092621 A1    May 15, 2003

Related U.S. Application Data

(60) Provisional application No. 60/308,386, filed on Jul. 27, 2001, provisional application No. 60/315,887, filed on Aug. 29, 2001.

(51) Int. Cl.
*C12N 9/48* (2006.01)
*C12Q 1/37* (2006.01)

(52) U.S. Cl. .......................................... 435/212; 435/24

(58) Field of Classification Search ..................... None
See application file for complete search history.

(56) References Cited

U.S. PATENT DOCUMENTS

| | | | |
|---|---|---|---|
| 4,419,446 A | 12/1983 | Howley et al. | 435/68 |
| 4,816,567 A | 3/1989 | Cabilly et al. | 530/387 |
| 6,689,599 B1 * | 2/2004 | Racie et al. | 435/226 |
| 2002/0115838 A1 * | 8/2002 | Friddle et al. | 536/23.1 |

FOREIGN PATENT DOCUMENTS

| | | |
|---|---|---|
| EP | 0 123 289 A2 | 10/1984 |
| EP | 0155476 A1 | 9/1985 |
| EP | 0 177 343 A1 | 4/1986 |
| EP | 1 134 286 A2 | 9/2001 |
| WO | WO 86/00639 | 1/1986 |
| WO | WO 01/59133 A1 | 8/2001 |
| WO | WO 01/75067 A2 | 10/2001 |
| WO | WO 01/83782 | 11/2001 |
| WO | WO 01/98468 A2 | 12/2001 |
| WO | WO 02/10216 A2 | 2/2002 |
| WO | WO 02/16564 A2 | 2/2002 |
| WO | WO 02/24927 A2 | 3/2002 |
| WO | WO 02/060942 A2 | 8/2002 |
| WO | WO 02/051995 A1 | 7/2004 |

OTHER PUBLICATIONS

Witkowski et al. (1999) Biochemistry 38:11643-11650.*
Branden et al. "Introduction to Protein Structure", Garland Publishing Inc., New York, p. 247.*
Tortorella et al. (2001) Osteoarthritis Cart 9:539-552.*
Arner et al. (1999) Ann N Y Acad Sci 878:92-107.*
"Introduction to Protein Structure Second Edition," Branden and Tooze, Garland Publishing Inc., New York, 1999, pp. 374-375.*
"Principles of X-ray Crystallography," Drenth, Springer, New York, 1995, p. 1.*
Kierzek et al. (2001) Biophys Chem 91:1-20.*

Abbaszade, et al., *J. Biol. Chem.*, 274:23443-23450 (1999).
Brandt, et al., *Pathogenesis of Osteoarthritis*, in Textbook of Rheumatology, WB Saunders Company, Philadelphia, PA, at 1355-1373 (1993).
Cal, et al., *Gene*, 283:49-62 (2002).
Clackson, et al., *Nature*, 352:624-628 (1991).
Flannery, et al., *J. Biol. Chem.*, 267:1008-1014 (1992).
Fosang, et al., *Biochem. J.*, 304:347-351 (1994).
Gething, et al., *Nature*, 293:620-625 (1981).
Gough, et al., *EMBO J.*, 4:645-653 (1985).
Hughes, et al., *Biochem. J.*, 305:799-804 (1995).
Jang, et al., *J. Virol.*, 63:1651-1660 (1989).
Kaufman, et al., *Mol. Cell Biol.*, 5:1750-1759 (1985).
Kaufman, et al., *J. Mol. Biol.*, 159:601-621 (1982).
Kaufman, et al., *Mol. Cell Biol.*, 2:1304-1319 (1982).
Kaufman, et al., *Nucleic Acid Res.*, 19:4485-4490 (1991).
Kaufman, *Proc. Natl. Acad. Sci. USA*, 82:689-693 (1985).
Köhler, et al., *Nature*, 256:495-499 (1975).
Laemmli, *Nature*, 227:680-685 (1970).
Littlefield, *Science*, 145:709-710 (1964).
Lohmander, et al., *Arthritis Rheum.*, 36:1214-1222 (1993).
MacLean, et al., *J. Rheumatol*, 25:2213-2218 (1998).
Maniatis, et al., *Molecular Cloning (A Laboratory Manual)*, Cold Spring Harbor Laboratory, at 387-389 (1982).
Marks, et al., *J. Mol. Biol.*, 222:581-597 (1991).
Mercuri, et al, *J. Bio. Chem.*, 274:32387-32395 (1999).
Miller, et al., *Genetic Engineering*, 8:277-298 (Plenum Press 1986).
Morinaga, et al., *Biotechnology*, 84:636-639 (1984).
Oakley, et al., *Anal. Biochem.*, 105:361-363 (1980).
Okayama, et al., *Mol. Cell. Biol.*, 2:161-170 (1982).
Sandy, et al., *J. Biol. Chem.*, 266:8683-8685 (1991).
Sandy, et al., *J. Clin. Invest.*, 89:1512-1516 (1992).
Taniguchi, et al., *Proc. Natl. Acad. Sci. USA*, 77:5230-5233 (1980).
Tortorella, et al., *Science*, 284:1664-1666 (1999).
Towbin, et al., *Proc. Natl. Acad. Sci. USA*, 76:4350-4354 (1979).
Wong, et al., *Science*, 228:810-815 (1985).
Bolz, H. et al., "Characterization of ADAMTS14, a Novel Member of the ADAMTS Metalloproteinase Family," Biochimica et Biophysica Acta, Dec. 30, 2001, 221-5, 1522, Elsevier Science.
Colige, A. et al., "Cloning and characterization of ADAMTS-14, a novel ADAMTS displaying high homology with ADAMTS-2 and ADAMTS-3," *J. Biol. Chem.*, 277(8):5756-5766 (2002).
Oi, V.T. and Herzenberg, L.A., "Immunoglobulin-Producing Hybrid Cell Lines," in Selected Methods in Cellular Immunity, Barbara B. Mishell and Stanley M. Shiigi (eds), W. H. Freeman & Co., San Francisco, CA, pp. 351-372 (1980).
Harlow et al., Antibodies: A Laboratory Manual, Cold Spring Harbor Laboratory Press, Cold Spring Harbor, New York (1988).

* cited by examiner

*Primary Examiner*—David J. Steadman
(74) *Attorney, Agent, or Firm*—Kirkpatrick & Lockhart Nicholson Graham LLP

(57) ABSTRACT

Novel aggrecanase proteins and the nucleotide sequences encoding them as well as processes for producing them are disclosed. Methods for developing inhibitors of the aggrecanase enzymes and antibodies to the enzymes for treatment of conditions characterized by the degradation of aggrecan are also disclosed.

2 Claims, No Drawings

SEQUENCE LISTING

```
<160> NUMBER OF SEQ ID NOS: 21

<210> SEQ ID NO 1
<211> LENGTH: 4080
<212> TYPE: DNA
<213> ORGANISM: Homo sapiens

<400> SEQUENCE: 1
atggctccac tccgcgcgct gctgtcctac ctgctgcctt tgcactgtgc gctctgcgcc      60
gccgcgggca gccggacccc agagctgcac ctctctggaa agctcagtga ctatggtgtg     120
acagtgccct gcagcacaga ctttcgggga cgcttcctct cccacgtggt gtctggccca     180
gcagcagcct ctgcaggag catggtagtg acacgccac ccacactacc acgacactcc       240
agtcacctcc gggtggctcg cagccctctg cacccaggag ggaccctgtg gcctggcagg     300
gtggggcgcc actccctcta cttcaatgtc actgttttcg ggaaggaact gcacttgcgc     360
ctgcggccca atcggaggtt ggtagtgcca ggatcctcag tggagtggca ggaggatttt     420
cgggagctgt tccggcagcc cttacggcag gagtgtgtgt acactggagg tgtcactgga     480
atgcctgggg cagctgttgc catcagcaac tgtgacggat tgtgtgcagg cccttgtgag     540
ctggcacagc agcctcaagg tcctgttggg cagctcttcc ctgccccaga gacatcagat     600
gccctggggc ctgatgccct gcgacggggt gacgggagct ggctgcacc gtgtttcccc      660 cttttgccttc agtgcctctt agaggaagcc gaggctcaag ttggggagga gatccagggt    720
catggaatag cagatgatgg cattcgcctt cctgcgctcc cttgcccctg cagtgtattc     780
gccaacagca gcctgggcag tcctgttaca atccgagtcc tccatgatgc tcgcctgtcg    840
gctgtactgt gtgttcatgc ctcttatttc tctcttccc gctgcttgcc gtccctggtt     900
caggcgggcc tcatccgcac agacagcacc gacttcttca ttgagcctct ggagcggggc    960
cagcaggaga aggaggccag cgggaggaca catgtggtgt accgccggga ggccgtccag   1020
caggagtggg cagaacctga cggggacctg cacaatgaag gagtttggct gtgggctgct   1080
gcgcttgcca ttggctcaga caccagggcc accagaagct gcctgcagtc ctttggcctg   1140
ggagaccttc ccaacctgct gggcctggtg ggggaccagc tgggcgacac agagcggaag   1200
cggcggcatg ccaagccagg cagctacagc atcgaggtgc tgctggtggt ggacgactcg   1260
gtggttcgct tccatggcaa ggagcatgtg cagaactatg tcctcacccc catgaatatc   1320
```

-continued

```
gtagatgaga tttaccacga tgagtccctg ggggttcata taaatattgc cctcgtccgc    1380
ttgatcatgg ttggctaccg acagtccctg agcctgatcg agcgcgggaa cccctcacgc    1440
agcctggagc aggtgtgtcg ctgggcacac tcccagcagc gccaggaccc cagccacgct    1500
gagcaccatg accacgttgt gttcctcacc cggcaggact ttgggccctc agggtatgca    1560
cccgtcactg gcatgtgtca cccctgagg agctgtgccc tcaaccatga ggatggcttc    1620
tcctcagcct tcgtgatagc tcatgagacc ggccacgtgc tcggcatgga gcatgacggt    1680
caggggaatg gctgtgcaga tgagaccagc ctgggcagcg tcatggcgcc cctggtgcag    1740
gctgccttcc accgcttcca ttggtcccgc tgcagcaagc tggagctcag ccgctacctc    1800
ccctcctacg actgcctcct cgatgacccc tttgatcctg cctggcccca gcccccagag    1860
ctgcctggga tcaactactc aatggatgag cagtgccgct ttgactttgg cagtggctac    1920
cagacctgct ggcattcag gacctttgag ccctgcaagc agctgtggtg cagccatcct    1980
gacaacccgt acttctgcaa gaccaagaag gggcccccgc tggatgggac tgagtgtgca    2040
cccggcaagt ggtgcttcaa aggtcactgc atctggaagt cgccggagca gacatatggc    2100
caggatggag gctggagctc ctggaccaag tttgggtcat gttcgcggtc atgtgggggc    2160
ggggtgcgat cccgcagccg gagctgcaac aacccctccc cagcctatgg aggccgcccg    2220
tgcttagggc ccatgttcga gtaccaggtc tgcaacagcg aggagtgccc tgggacctac    2280
gaggacttcc gggcccagca gtgtgccaag cgcaactcgt actatgtgca ccagaatgcc    2340
aagcacagct gggtgcccta cgagcctgac gatgacgccc agaagtgtga gctgatctgc    2400
cagtcggcgg acacggggga cgtggtgttc atgaaccagg tggttcacga tgggacacgc    2460
tgcagctacc gggacccata cagcgtctgt gcgcgtggcg agtgtgtgcc tgtcggctgt    2520
gacaaggagg tggggtccat gaaggcggat gacaagtgtg gagtctgcgg gggtgacaac    2580
tcccactgca ggactgtgaa ggggacgctg gcaaggcct ccaagcaggc aggagctctc    2640
aagctggtgc agatcccagc aggtgccagg cacatccaga ttgaggcact ggagaagtcc    2700
ccccaccgca ttgtggtgaa gaaccaggtc accggcagct tcatcctcaa ccccaagggc    2760
aaggaagcca agccggac cttcaccgcc atgggcctgg agtgggagga tgcggtggag    2820
gatgccaagg aaagcctcaa gaccagcggg cccctgcctg aagccattgc catcctggct    2880
ctccccccaa ctgagggtgg ccccgcagc agcctggcct acaagtacgt catccatgag    2940
gacctgctgc cccttatcgg gagcaacaat gtgctcctgg aggagatgga cacctatgag    3000
tgggcgctca agagctgggc cccctgcagc aaggcctgtg gaggagggat ccagttcacc    3060
aaatacggct gccggcgcag acgagaccac acatggtgc agcgacacct gtgtgaccac    3120
aagaagaggc ccaagcccat ccgccggcgc tgcaaccagc acccgtgctc tcagcctgtg    3180
tgggtgacgg aggagtgggg tgcctgcagc cggagctgtg gaagctgggg ggtgcagaca    3240
cgggggatac agtgcctgat gcccctctcc aatggaaccc acaaggtcat gccggccaaa    3300
gcctgtgccg ggaccggcc tgaggcccga cggccctgtc tccgagtgcc ctgcccagcc    3360
cagtggaggc tgggagcctg gtcccagtgc tctgccacct gtgagagggg catccagcag    3420
cggcaggtgg tgtgcaggac caacgccaac agcctcgggc attgcgaggg ggataggcca    3480
gacactgtcc aggtctgcag cctgcctgcc tgtgaggaa atcaccagaa ctccacggtg    3540
agggccgatg tctgggaact tgggacgcca gaggggcagt gggtgccaca atctgaaccc    3600
ctacatccca ttaacaagat atcatcaacg gagccctgca cggagacag gtctgtcttc    3660
```

-continued

```
tgccagatgg aagtgctcga tcgctactgc tccattcccg gctaccaccg gctctgctgt    3720
gtgtcctgca tcaagaaggc ctcgggcccc aaccctggcc cagaccctgg cccaacctca    3780 ctgccccct tctccactcc tggaagcccc ttaccaggac cccaggaccc tgcagatgct    3840
gcagagcctc ctggaaagcc aacgggatca gaggaccatc agcatggccg agccacacag    3900
ctcccaggag ctctggatac aagctcccca gggacccagc atcccttgc ccctgagaca    3960 ccaatccctg gagcatcctg gagcatctcc cctaccaccc ccgggggct gccttgggc    4020 tggactcaga cacctacgcc agtccctgag gacaaagggc aacctggaga agacctgaga   4080
```

<210> SEQ ID NO 2
<211> LENGTH: 1233
<212> TYPE: PRT
<213> ORGANISM: Homo sapiens

<400> SEQUENCE: 2

```
Met Ala Pro Leu Arg Ala Leu Leu Ser Tyr Leu Leu Pro Leu His Cys
  1               5                  10                  15

Ala Leu Cys Ala Ala Ala Gly Ser Arg Thr Pro Glu Leu His Leu Ser
             20                  25                  30

Gly Lys Leu Ser Asp Tyr Gly Val Thr Val Pro Cys Ser Thr Asp Phe
         35                  40                  45

Arg Gly Arg Phe Leu Ser His Val Val Ser Gly Pro Ala Ala Ala Ser
     50                  55                  60

Ala Gly Ser Met Val Val Asp Thr Pro Pro Thr Leu Pro Arg His Ser
 65                  70                  75                  80

Ser His Leu Arg Val Ala Arg Ser Pro Leu His Pro Gly Gly Thr Leu
                 85                  90                  95

Trp Pro Gly Arg Val Gly Arg His Ser Leu Tyr Phe Asn Val Thr Val
            100                 105                 110

Phe Gly Lys Glu Leu His Leu Arg Leu Arg Pro Asn Arg Arg Leu Val
        115                 120                 125

Val Pro Gly Ser Ser Val Glu Trp Gln Glu Asp Phe Arg Glu Leu Phe
    130                 135                 140

Arg Gln Pro Leu Arg Gln Glu Cys Val Tyr Thr Gly Val Thr Gly
145                 150                 155                 160

Met Pro Gly Ala Ala Val Ala Ile Ser Asn Cys Asp Gly Leu Ala Gly
                165                 170                 175

Leu Ile Arg Thr Asp Ser Thr Asp Phe Phe Ile Glu Pro Leu Glu Arg
            180                 185                 190

Gly Gln Gln Glu Lys Glu Ala Ser Gly Arg Thr His Val Val Tyr Arg
        195                 200                 205

Arg Glu Ala Val Gln Gln Glu Trp Ala Glu Pro Asp Gly Asp Leu His
    210                 215                 220

Asn Glu Gly Val Trp Leu Trp Ala Ala Leu Ala Ile Gly Ser Asp
225                 230                 235                 240

Thr Arg Ala Thr Arg Ser Cys Leu Gln Ser Phe Gly Leu Gly Asp Leu
                245                 250                 255

Pro Asn Leu Leu Gly Leu Val Gly Asp Gln Leu Gly Asp Thr Glu Arg
            260                 265                 270

Lys Arg His Ala Lys Pro Gly Ser Tyr Ser Ile Glu Val Leu Leu
        275                 280                 285

Val Val Asp Asp Ser Val Val Arg Phe His Gly Lys Glu His Val Gln
    290                 295                 300
```

-continued

```
Asn Tyr Val Leu Thr Leu Met Asn Ile Val Asp Glu Ile Tyr His Asp
305                 310                 315                 320

Glu Ser Leu Gly Val His Ile Asn Ile Ala Leu Val Arg Leu Ile Met
            325                 330                 335

Val Gly Tyr Arg Gln Ser Leu Ser Leu Ile Glu Arg Gly Asn Pro Ser
        340                 345                 350

Arg Ser Leu Glu Gln Val Cys Arg Trp Ala His Ser Gln Gln Arg Gln
    355                 360                 365

Asp Pro Ser His Ala Glu His His Asp His Val Val Phe Leu Thr Arg
370                 375                 380

Gln Asp Phe Gly Pro Ser Gly Tyr Ala Pro Val Thr Gly Met Cys His
385                 390                 395                 400

Pro Leu Arg Ser Cys Ala Leu Asn His Glu Asp Gly Phe Ser Ser Ala
                405                 410                 415

Phe Val Ile Ala His Glu Thr Gly His Val Leu Gly Met Glu His Asp
            420                 425                 430

Gly Gln Gly Asn Gly Cys Ala Asp Glu Thr Ser Leu Gly Ser Val Met
        435                 440                 445

Ala Pro Leu Val Gln Ala Ala Phe His Arg Phe His Trp Ser Arg Cys
    450                 455                 460

Ser Lys Leu Glu Leu Ser Arg Tyr Leu Pro Ser Tyr Asp Cys Leu Leu
465                 470                 475                 480

Asp Asp Pro Phe Asp Pro Ala Trp Pro Gln Pro Pro Glu Leu Pro Gly
                485                 490                 495

Ile Asn Tyr Ser Met Asp Glu Gln Cys Arg Phe Asp Phe Gly Ser Gly
            500                 505                 510

Tyr Gln Thr Cys Leu Ala Phe Arg Thr Phe Glu Pro Cys Lys Gln Leu
        515                 520                 525

Trp Cys Ser His Pro Asp Asn Pro Tyr Phe Cys Lys Thr Lys Lys Gly
530                 535                 540

Pro Pro Leu Asp Gly Thr Glu Cys Ala Pro Gly Lys Trp Cys Phe Lys
545                 550                 555                 560

Gly His Cys Ile Trp Lys Ser Pro Glu Gln Thr Tyr Gly Gln Asp Gly
                565                 570                 575

Gly Trp Ser Ser Trp Thr Lys Phe Gly Ser Cys Ser Arg Ser Cys Gly
            580                 585                 590

Gly Gly Val Arg Ser Arg Ser Arg Ser Cys Asn Asn Pro Ser Pro Ala
        595                 600                 605

Tyr Gly Gly Arg Pro Cys Leu Gly Pro Met Phe Glu Tyr Gln Val Cys
    610                 615                 620

Asn Ser Glu Glu Cys Pro Gly Thr Tyr Glu Asp Phe Arg Ala Gln Gln
625                 630                 635                 640

Cys Ala Lys Arg Asn Ser Tyr Tyr Val His Gln Asn Ala Lys His Ser
                645                 650                 655

Trp Val Pro Tyr Glu Pro Asp Asp Ala Gln Lys Cys Glu Leu Ile
            660                 665                 670

Cys Gln Ser Ala Asp Thr Gly Asp Val Val Phe Met Asn Gln Val Val
        675                 680                 685

His Asp Gly Thr Arg Cys Ser Tyr Arg Asp Pro Tyr Ser Val Cys Ala
    690                 695                 700

Arg Gly Glu Cys Val Pro Val Gly Cys Asp Lys Glu Val Gly Ser Met
705                 710                 715                 720

Lys Ala Asp Asp Lys Cys Gly Val Cys Gly Gly Asp Asn Ser His Cys
```

-continued

```
                725                 730                 735
Arg Thr Val Lys Gly Thr Leu Gly Lys Ala Ser Lys Gln Ala Gly Ala
            740                 745                 750
Leu Lys Leu Val Gln Ile Pro Ala Gly Ala Arg His Ile Gln Ile Glu
            755                 760                 765
Ala Leu Glu Lys Ser Pro His Arg Ile Val Lys Asn Gln Val Thr
            770                 775                 780
Gly Ser Phe Ile Leu Asn Pro Lys Gly Lys Glu Ala Thr Ser Arg Thr
785                 790                 795                 800
Phe Thr Ala Met Gly Leu Glu Trp Glu Asp Ala Val Glu Asp Ala Lys
                805                 810                 815
Glu Ser Leu Lys Thr Ser Gly Pro Leu Pro Glu Ala Ile Ala Ile Leu
            820                 825                 830
Ala Leu Pro Pro Thr Glu Gly Gly Pro Arg Ser Ser Leu Ala Tyr Lys
            835                 840                 845
Tyr Val Ile His Glu Asp Leu Leu Pro Leu Ile Gly Ser Asn Asn Val
            850                 855                 860
Leu Leu Glu Glu Met Asp Thr Tyr Glu Trp Ala Leu Lys Ser Trp Ala
865                 870                 875                 880
Pro Cys Ser Lys Ala Cys Gly Gly Ile Gln Phe Thr Lys Tyr Gly
                885                 890                 895
Cys Arg Arg Arg Asp His His Met Val Gln Arg His Leu Cys Asp
                900                 905                 910
His Lys Lys Arg Pro Lys Pro Ile Arg Arg Cys Asn Gln His Pro
            915                 920                 925
Cys Ser Gln Pro Val Trp Val Thr Glu Glu Trp Gly Ala Cys Ser Arg
            930                 935                 940
Ser Cys Gly Lys Leu Gly Val Gln Thr Arg Gly Ile Gln Cys Leu Met
945                 950                 955                 960
Pro Leu Ser Asn Gly Thr His Lys Val Met Pro Ala Lys Ala Cys Ala
                965                 970                 975
Gly Asp Arg Pro Glu Ala Arg Arg Pro Cys Leu Arg Val Pro Cys Pro
            980                 985                 990
Ala Gln Trp Arg Leu Gly Ala Trp Ser Gln Cys Ser Ala Thr Cys Gly
            995                 1000                1005
Glu Gly Ile Gln Gln Arg Gln Val Val Cys Arg Thr Asn Ala Asn Ser
            1010                1015                1020
Leu Gly His Cys Glu Gly Asp Arg Pro Asp Thr Val Gln Val Cys Ser
1025                1030                1035                1040
Leu Pro Ala Cys Gly Gly Asn His Gln Asn Ser Thr Val Arg Ala Asp
                1045                1050                1055
Val Trp Glu Leu Gly Thr Pro Glu Gly Gln Trp Val Pro Gln Ser Glu
            1060                1065                1070
Pro Leu His Pro Ile Asn Lys Ile Ser Ser Thr Glu Pro Cys Thr Gly
            1075                1080                1085
Asp Arg Ser Val Phe Cys Gln Met Glu Val Leu Asp Arg Tyr Cys Ser
            1090                1095                1100
Ile Pro Gly Tyr His Arg Leu Cys Cys Val Ser Cys Ile Lys Lys Ala
1105                1110                1115                1120
Ser Gly Pro Asn Pro Gly Pro Asp Gly Pro Thr Ser Leu Pro Pro
            1125                1130                1135
Phe Ser Thr Pro Gly Ser Pro Leu Pro Gly Pro Gln Asp Pro Ala Asp
            1140                1145                1150
```

Ala Ala Glu Pro Pro Gly Lys Pro Thr Gly Ser Glu Asp His Gln His
        1155                1160                1165

Gly Arg Ala Thr Gln Leu Pro Gly Ala Leu Asp Thr Ser Ser Pro Gly
    1170                1175                1180

Thr Gln His Pro Phe Ala Pro Glu Thr Pro Ile Pro Gly Ala Ser Trp
1185                1190                1195                1200

Ser Ile Ser Pro Thr Thr Pro Gly Gly Leu Pro Trp Gly Trp Thr Gln
            1205                1210                1215

Thr Pro Thr Pro Val Pro Glu Asp Lys Gly Gln Pro Gly Glu Asp Leu
        1220                1225                1230

Arg

<210> SEQ ID NO 3
<211> LENGTH: 3691
<212> TYPE: DNA
<213> ORGANISM: Homo sapiens

<400> SEQUENCE: 3
gaattcccac catggctcca ctccgcgcgc tgctgtccta cctgctgcct ttgcactgtg      60
cgctctgcgc cgccgcgggc agccggaccc agagctgca cctctctgga agctcagtg      120 actatggtgt gacagtgccc tgcagcacag actttcgggg acgcttcctc tcccacgtgg    180
tgtctggccc agcagcagcc tctgcaggga gcatggtagt ggacacgcca cccacactac    240
cacgacactc cagtcacctc cggtggctc gcagccctct gcacccagga gggaccctgt     300
ggcctggcag ggtggggcgc cactccctct acttcaatgt cactgttttc gggaaggaac    360
tgcacttgcg cctgcggccc aatcggaggt tggtagtgcc aggatcctca gtggagtggc    420
aggaggattt tcgggagctg ttccggcagc ccttacggca ggagtgtgtg tacactggag    480
gtgtcactgg aatgcctggg gcagctgttg ccatcagcaa ctgtgacgga ttggcgggcc    540
tcatccgcac agacagcacc gacttcttca ttgagcctct ggagcggggc cagcaggaga    600
aggaggccag cgggaggaca catgtggtgt accgccggga ggccgtccag caggagtggg    660
cagaacctga cggggacctg cacaatgaag cctttggcct gggagacctt cccaacctgc    720
tgggcctggt ggggaccag ctgggcgaca cagagcggaa cggcggcat gccaagccag      780 gcagctacag catcgaggtg ctactggtgg tggacgactc ggtggttcgc ttccatggca    840
aggagcatgt gcagaactat gtcctcaccc tcatgaatat cgtagatgag atttaccacg    900
atgagtccct gggggttcat ataaatattg ccctcgtccg cttgatcatg gttggctacc    960
gacagtccct gagcctgatc gagcgcggga accctcacg cagcctggag caggtgtgtc     1020
gctgggcaca ctcccagcag cgccaggacc ccagccacgc tgagcaccat gaccacgttg    1080
tgttcctcac ccggcaggac tttgggccct cagggtatgc accgtcact ggcatgtgtc     1140 accccctgag gagctgtgcc ctcaaccatg aggatggctt ctcctcagcc ttcgtgatag    1200
ctcatgagac cggccacgtg tcggcatgg agcatgacgg tcaggggaat ggctgtgcag     1260
atgagaccaa cctgggcagc gtcatggcgc cctggtgca ggctgccttc caccgcttcc     1320
attggtcccg ctgcagcaag ctggagctca gccgctacct ccctcctac gactgcctcc    1380 tcgatgaccc ctttgatcct gcctggcccc agccccaga gctgcctggg atcaactact    1440
caatggatga gcagtgccgc tttgactttg cagtggcta ccagacctgc ttggcattta    1500 ggaccttga gccctgcaag cagctgtggt gcagccatcc tgacaacccg tacttctgca    1560
agaccaagaa ggggcccccg ctggatggga ctgagtgtgc accggcaag tggtgcttca    1620

-continued

```
aaggtcactg catctggaag tcgccggagc agacatatgg ccaggatgga ggctggagct    1680
cctggaccaa gtttgggtca tgttcgcggt catgtggggg cggggtgcga tcccgcagcc    1740
ggagctgcaa caacccctcc ccagcctatg gaggccgccc gtgcttaggg cccatgttcg    1800
agtaccaggt ctgcaacagc gaggagtgcc ctgggaccta cgaggacttc cgggcccagc    1860
agtgtgccaa gcgcaactcc tactatgtgc accagaatgc caagcacagc tgggtgccct    1920
acgagcctga cgatgacgcc cagaagtgtg agctgatctg ccagtcggcg gacacggggg    1980
acgtggtgtt catgaaccag gtggttcacg atgggacacg ctgcagctac cgggacccat    2040
acagcgtctg tgcgcgtggc gagtgtgtgc ctgtcggctg tgacaaggag gtggggtcca    2100
tgaaggcgga tgacaagtgt ggagtctgcg ggggtgacaa ctcccactgc aggactgtga    2160
aggggacgct gggcaaggcc tccaagcagg caggagctct caagctggtg cagatcccag    2220
caggtgccag gcacatccag attgaggcac tggagaagtc cccccaccgc attgtggtga    2280
agaaccaggt caccggcagc ttcatcctca accccaaggg caaggaagcc acaagccgga    2340
ccttcaccgc catgggcctg gagtgggagg atgcggtgga ggatgccaag gaaagcctca    2400
agaccagcgg gccctgcct gaagccattg ccatcctggc tctcccccca actgagggtg    2460
ccccccgcag cagcctggcc tacaagtacg tcatccatga ggacctgctg ccccttatcg    2520
ggagcaacaa tgtgctcctg gaggagatgg acacctatga gtgggcgctc aagagctggg    2580 cccctgcag caaggcctgt ggaggaggga tccagttcac caaatacggc tgccggcgca    2640
gacgagacca ccacatggtg cagcgacacc tgtgtgacca agaagaggg cccaagccca    2700 tccgccggcg ctgcaaccag cacccgtgct ctcagcctgt gtgggtgacg gaggagtggg    2760
gtgcctgcag ccggagctgt gggaagctgg gggtgcagac acgggggata cagtgcctga    2820
tgccccttct caatggaacc cacaaggtca tgccggccaa agcctgtgcc ggggaccggc    2880
ctgaggcccg acgccctgt ctccgagtgc cctgcccagc ccagtggagg ctgggagcct    2940
ggtcccagtg ctctgccacc tgtggagagg gcatccagca gcggcaggtg gtgtgcagga    3000
ccaacgccaa cagcctcggg cattgcgagg gggataggcc agacactgtc caggtctgca    3060
gcctgcctgc ctgtggagga atcaccagga actccacggt gagggccgat gtctgggaac    3120
ttgggacgcc agaggggcag tgggtgccac aatctgaacc cctacatccc attaacaaga    3180
tatcatcaac ggagccctgc acgggagaca ggtctgtctt ctgccagatg gaggtgctcg    3240
atcgctactc ctccattccc ggctaccacc ggctctgctg tgtgtcctgc atcaagaagg    3300
cctcgggccc caaccctggc ccagaccctg gccaacctc actgccccc ttctccactc    3360 ctggaagccc cttaccagga ccccaggacc ctgcagatgc tgcggagcct cctgaaaagc    3420
caacgggatc agaggaccat cagcatggcc gagccacaca gctcccagga gctctggata    3480
caagctcccc agggacccag catcccttg ccccctgagac accaatccct ggagcatcct    3540
ggagcatctc ccctaccacc cccgggggggc tgccttgggg ctggactcag acacctacgc    3600
cagtccctga ggacaaaggg caacctggag aagacctgag acatcccggc accagcctcc    3660
ctgctgcctc cccggtgaca tgagcggccg c                                  3691
```

<210> SEQ ID NO 4
<211> LENGTH: 1223
<212> TYPE: PRT
<213> ORGANISM: Homo sapiens

<400> SEQUENCE: 4

-continued

```
Met Ala Pro Leu Arg Ala Leu Leu Ser Tyr Leu Leu Pro Leu His Cys
 1               5                   10                  15

Ala Leu Cys Ala Ala Gly Ser Arg Thr Pro Glu Leu His Leu Ser
            20                  25                  30

Gly Lys Leu Ser Asp Tyr Gly Val Thr Val Pro Cys Ser Thr Asp Phe
        35                  40                  45

Arg Gly Arg Phe Leu Ser His Val Val Ser Gly Pro Ala Ala Ser
    50                  55                  60

Ala Gly Ser Met Val Val Asp Thr Pro Pro Thr Leu Pro Arg His Ser
65                  70                  75                  80

Ser His Leu Arg Val Ala Arg Ser Pro Leu His Pro Gly Gly Thr Leu
                85                  90                  95

Trp Pro Gly Arg Val Gly Arg His Ser Leu Tyr Phe Asn Val Thr Val
            100                 105                 110

Phe Gly Lys Glu Leu His Leu Arg Leu Arg Pro Asn Arg Arg Leu Val
        115                 120                 125

Val Pro Gly Ser Ser Val Glu Trp Gln Glu Asp Phe Arg Glu Leu Phe
    130                 135                 140

Arg Gln Pro Leu Arg Gln Glu Cys Val Tyr Thr Gly Gly Val Thr Gly
145                 150                 155                 160

Met Pro Gly Ala Ala Val Ala Ile Ser Asn Cys Asp Gly Leu Ala Gly
                165                 170                 175

Leu Ile Arg Thr Asp Ser Thr Asp Phe Phe Ile Glu Pro Leu Glu Arg
            180                 185                 190

Gly Gln Gln Glu Lys Glu Ala Ser Gly Arg Thr His Val Val Tyr Arg
        195                 200                 205

Arg Glu Ala Val Gln Gln Glu Trp Ala Glu Pro Asp Gly Asp Leu His
    210                 215                 220

Asn Glu Ala Phe Gly Leu Gly Asp Leu Pro Asn Leu Leu Gly Leu Val
225                 230                 235                 240

Gly Asp Gln Leu Gly Asp Thr Glu Arg Lys Arg Arg His Ala Lys Pro
                245                 250                 255

Gly Ser Tyr Ser Ile Glu Val Leu Leu Val Val Asp Asp Ser Val Val
            260                 265                 270

Arg Phe His Gly Lys Glu His Val Gln Asn Tyr Val Leu Thr Leu Met
        275                 280                 285

Asn Ile Val Asp Glu Ile Tyr His Asp Glu Ser Leu Gly Val His Ile
290                 295                 300

Asn Ile Ala Leu Val Arg Leu Ile Met Val Gly Tyr Arg Gln Ser Leu
305                 310                 315                 320

Ser Leu Ile Glu Arg Gly Asn Pro Ser Arg Ser Leu Glu Gln Val Cys
                325                 330                 335

Arg Trp Ala His Ser Gln Gln Arg Gln Asp Pro Ser His Ala Glu His
            340                 345                 350

His Asp His Val Val Phe Leu Thr Arg Gln Asp Phe Gly Pro Ser Gly
        355                 360                 365

Tyr Ala Pro Val Thr Gly Met Cys His Pro Leu Arg Ser Cys Ala Leu
    370                 375                 380

Asn His Glu Asp Gly Phe Ser Ser Ala Phe Val Ile Ala His Glu Thr
385                 390                 395                 400

Gly His Val Leu Gly Met Glu His Asp Gly Gln Gly Asn Gly Cys Ala
                405                 410                 415

Asp Glu Thr Ser Leu Gly Ser Val Met Ala Pro Leu Val Gln Ala Ala
```

-continued

```
                420                 425                 430
Phe His Arg Phe His Trp Ser Arg Cys Ser Lys Leu Glu Leu Ser Arg
            435                 440                 445

Tyr Leu Pro Ser Tyr Asp Cys Leu Leu Asp Asp Pro Phe Asp Pro Ala
        450                 455                 460

Trp Pro Gln Pro Pro Glu Leu Pro Gly Ile Asn Tyr Ser Met Asp Glu
465                 470                 475                 480

Gln Cys Arg Phe Asp Phe Gly Ser Gly Tyr Gln Thr Cys Leu Ala Phe
                485                 490                 495

Arg Thr Phe Glu Pro Cys Lys Gln Leu Trp Cys Ser His Pro Asp Asn
            500                 505                 510

Pro Tyr Phe Cys Lys Thr Lys Lys Gly Pro Pro Leu Asp Gly Thr Glu
        515                 520                 525

Cys Ala Pro Gly Lys Trp Cys Phe Lys Gly His Cys Ile Trp Lys Ser
    530                 535                 540

Pro Glu Gln Thr Tyr Gly Gln Asp Gly Gly Trp Ser Ser Trp Thr Lys
545                 550                 555                 560

Phe Gly Ser Cys Ser Arg Ser Cys Gly Gly Val Arg Ser Arg Ser
                565                 570                 575

Arg Ser Cys Asn Asn Pro Ser Pro Ala Tyr Gly Gly Arg Pro Cys Leu
            580                 585                 590

Gly Pro Met Phe Glu Tyr Gln Val Cys Asn Ser Glu Cys Pro Gly
        595                 600                 605

Thr Tyr Glu Asp Phe Arg Ala Gln Gln Cys Ala Lys Arg Asn Ser Tyr
    610                 615                 620

Tyr Val His Gln Asn Ala Lys His Ser Trp Val Pro Tyr Glu Pro Asp
625                 630                 635                 640

Asp Asp Ala Gln Lys Cys Glu Leu Ile Cys Gln Ser Ala Asp Thr Gly
                645                 650                 655

Asp Val Val Phe Met Asn Gln Val Val His Asp Gly Thr Arg Cys Ser
            660                 665                 670

Tyr Arg Asp Pro Tyr Ser Val Cys Ala Arg Gly Glu Cys Val Pro Val
        675                 680                 685

Gly Cys Asp Lys Glu Val Gly Ser Met Lys Ala Asp Asp Lys Cys Gly
    690                 695                 700

Val Cys Gly Gly Asp Asn Ser His Cys Arg Thr Val Lys Gly Thr Leu
705                 710                 715                 720

Gly Lys Ala Ser Lys Gln Ala Gly Ala Leu Lys Leu Val Gln Ile Pro
                725                 730                 735

Ala Gly Ala Arg His Ile Gln Ile Glu Ala Leu Glu Lys Ser Pro His
            740                 745                 750

Arg Ile Val Val Lys Asn Gln Val Thr Gly Ser Phe Ile Leu Asn Pro
        755                 760                 765

Lys Gly Lys Glu Ala Thr Ser Arg Thr Phe Thr Ala Met Gly Leu Glu
    770                 775                 780

Trp Glu Asp Ala Val Glu Asp Ala Lys Glu Ser Leu Lys Thr Ser Gly
785                 790                 795                 800

Pro Leu Pro Glu Ala Ile Ala Ile Leu Ala Leu Pro Pro Thr Glu Gly
                805                 810                 815

Gly Pro Arg Ser Ser Leu Ala Tyr Lys Tyr Val Ile His Glu Asp Leu
            820                 825                 830

Leu Pro Leu Ile Gly Ser Asn Asn Val Leu Leu Glu Glu Met Asp Thr
        835                 840                 845
```

Tyr Glu Trp Ala Leu Lys Ser Trp Ala Pro Cys Ser Lys Ala Cys Gly
    850                 855                 860

Gly Gly Ile Gln Phe Thr Lys Tyr Gly Cys Arg Arg Arg Asp His
865                 870                 875                 880

His Met Val Gln Arg His Leu Cys Asp His Lys Arg Pro Lys Pro
                885                 890                 895

Ile Arg Arg Cys Asn Gln His Pro Cys Ser Gln Pro Val Trp Val
                900                 905                 910

Thr Glu Glu Trp Gly Ala Cys Ser Arg Ser Cys Gly Lys Leu Gly
                915                 920                 925

Gln Thr Arg Gly Ile Gln Cys Leu Met Pro Leu Ser Asn Gly Thr His
    930                 935                 940

Lys Val Met Pro Ala Lys Ala Cys Ala Gly Asp Arg Pro Glu Ala Arg
945                 950                 955                 960

Arg Pro Cys Leu Arg Val Pro Cys Pro Ala Gln Trp Arg Leu Gly Ala
                965                 970                 975

Trp Ser Gln Cys Ser Ala Thr Cys Gly Glu Gly Ile Gln Gln Arg Gln
                980                 985                 990

Val Val Cys Arg Thr Asn Ala Asn Ser Leu Gly His Cys Glu Gly Asp
            995                 1000                1005

Arg Pro Asp Thr Val Gln Val Cys Ser Leu Pro Ala Cys Gly Gly Asn
    1010                1015                1020

His Gln Asn Ser Thr Val Arg Ala Asp Val Trp Glu Leu Gly Thr Pro
1025                1030                1035                1040

Glu Gly Gln Trp Val Pro Gln Ser Glu Pro Leu His Pro Ile Asn Lys
                1045                1050                1055

Ile Ser Ser Thr Glu Pro Cys Thr Gly Asp Arg Ser Val Phe Cys Gln
                1060                1065                1070

Met Glu Val Leu Asp Arg Tyr Cys Ser Ile Pro Gly Tyr His Arg Leu
            1075                1080                1085

Cys Cys Val Ser Cys Ile Lys Lys Ala Ser Gly Pro Asn Pro Gly Pro
    1090                1095                1100

Asp Pro Gly Pro Thr Ser Leu Pro Pro Phe Ser Thr Pro Gly Ser Pro
1105                1110                1115                1120

Leu Pro Gly Pro Gln Asp Pro Ala Asp Ala Glu Pro Pro Gly Lys
                1125                1130                1135

Pro Thr Gly Ser Glu Asp His Gln His Gly Arg Ala Thr Gln Leu Pro
                1140                1145                1150

Gly Ala Leu Asp Thr Ser Ser Pro Gly Thr Gln His Pro Phe Ala Pro
        1155                1160                1165

Glu Thr Pro Ile Pro Gly Ala Ser Trp Ser Ile Ser Pro Thr Thr Pro
    1170                1175                1180

Gly Gly Leu Pro Trp Gly Trp Thr Gln Thr Pro Thr Pro Val Pro Glu
1185                1190                1195                1200

Asp Lys Gly Gln Pro Gly Glu Asp Leu Arg His Pro Gly Thr Ser Leu
                1205                1210                1215

Pro Ala Ala Ser Pro Val Thr
                1220

<210> SEQ ID NO 5
<211> LENGTH: 1360
<212> TYPE: PRT
<213> ORGANISM: Unknown Organism
<220> FEATURE:

<223> OTHER INFORMATION: Description of Unknown Organism: Genscan 2 peptide sequence

<400> SEQUENCE: 5

```
Met Ala Pro Leu Arg Ala Leu Leu Ser Tyr Leu Leu Pro Leu His Cys
 1               5                  10                  15

Ala Leu Cys Ala Ala Ala Gly Ser Arg Thr Pro Glu Leu His Leu Ser
            20                  25                  30

Gly Lys Leu Ser Asp Tyr Gly Val Thr Val Pro Cys Ser Thr Asp Phe
        35                  40                  45

Arg Gly Arg Phe Leu Ser His Val Val Ser Gly Pro Ala Ala Ala Ser
    50                  55                  60

Ala Gly Ser Met Val Val Asp Thr Pro Pro Thr Leu Pro Arg His Ser
65                  70                  75                  80

Ser His Leu Arg Val Ala Arg Ser Pro Leu His Pro Gly Gly Thr Leu
                85                  90                  95

Trp Pro Gly Arg Val Gly Arg His Ser Leu Tyr Phe Asn Val Thr Val
            100                 105                 110

Phe Gly Lys Glu Leu His Leu Arg Leu Arg Pro Asn Arg Arg Leu Val
        115                 120                 125

Val Pro Gly Ser Ser Val Glu Trp Gln Glu Asp Phe Arg Glu Leu Phe
    130                 135                 140

Arg Gln Pro Leu Arg Gln Glu Cys Val Tyr Thr Gly Gly Val Thr Gly
145                 150                 155                 160

Met Pro Gly Ala Ala Val Ala Ile Ser Asn Cys Asp Gly Leu Cys Ala
                165                 170                 175

Gly Pro Cys Glu Leu Ala Gln Gln Pro Gln Gly Pro Val Gly Gln Leu
            180                 185                 190

Phe Pro Ala Pro Glu Thr Ser Asp Ala Leu Gly Pro Asp Ala Leu Arg
        195                 200                 205

Arg Gly Asp Gly Ser Leu Ala Ala Pro Cys Phe Pro Leu Cys Leu Gln
    210                 215                 220

Cys Leu Leu Glu Glu Ala Glu Ala Gln Val Gly Glu Glu Ile Gln Gly
225                 230                 235                 240

His Gly Ile Ala Asp Asp Gly Ile Arg Leu Pro Ala Leu Pro Cys Pro
                245                 250                 255

Cys Ser Val Phe Ala Asn Ser Ser Leu Gly Ser Pro Val Thr Ile Arg
            260                 265                 270

Val Leu His Asp Ala Arg Leu Ser Ala Val Leu Cys Val His Ala Ser
        275                 280                 285

Tyr Phe Ser Leu Ser Arg Cys Leu Pro Ser Leu Val Gln Ala Gly Leu
    290                 295                 300

Ile Arg Thr Asp Ser Thr Asp Phe Phe Ile Glu Pro Leu Glu Arg Gly
305                 310                 315                 320

Gln Gln Glu Lys Glu Ala Ser Gly Arg Thr His Val Val Tyr Arg Arg
                325                 330                 335

Glu Ala Val Gln Gln Glu Trp Ala Glu Pro Asp Gly Asp Leu His Asn
            340                 345                 350

Glu Gly Val Trp Leu Trp Ala Ala Ala Leu Ala Ile Gly Ser Asp Thr
        355                 360                 365

Arg Ala Thr Arg Ser Cys Leu Gln Ser Phe Gly Leu Gly Asp Leu Pro
    370                 375                 380

Asn Leu Leu Gly Leu Val Gly Asp Gln Leu Gly Asp Thr Glu Arg Lys
385                 390                 395                 400
```

```
Arg Arg His Ala Lys Pro Gly Ser Tyr Ser Ile Glu Val Leu Leu Val
            405                 410                 415
Val Asp Asp Ser Val Val Arg Phe His Gly Lys Glu His Val Gln Asn
            420                 425                 430
Tyr Val Leu Thr Leu Met Asn Ile Val Asp Glu Ile Tyr His Asp Glu
            435                 440                 445
Ser Leu Gly Val His Ile Asn Ile Ala Leu Val Arg Leu Ile Met Val
            450                 455                 460
Gly Tyr Arg Gln Ser Leu Ser Leu Ile Glu Arg Gly Asn Pro Ser Arg
465                 470                 475                 480
Ser Leu Glu Gln Val Cys Arg Trp Ala His Ser Gln Arg Gln Asp
            485                 490                 495
Pro Ser His Ala Glu His His Asp Val Val Phe Leu Thr Arg Gln
            500                 505                 510
Asp Phe Gly Pro Ser Gly Tyr Ala Pro Val Thr Gly Met Cys His Pro
            515                 520                 525
Leu Arg Ser Cys Ala Leu Asn His Glu Asp Gly Phe Ser Ser Ala Phe
            530                 535                 540
Val Ile Ala His Glu Thr Gly His Val Leu Gly Met Glu His Asp Gly
545                 550                 555                 560
Gln Gly Asn Gly Cys Ala Asp Glu Thr Ser Leu Gly Ser Val Met Ala
            565                 570                 575
Pro Leu Val Gln Ala Ala Phe His Arg Phe His Trp Ser Arg Cys Ser
            580                 585                 590
Lys Leu Glu Leu Ser Arg Tyr Leu Pro Ser Tyr Asp Cys Leu Leu Asp
            595                 600                 605
Asp Pro Phe Asp Pro Ala Trp Pro Gln Pro Pro Glu Leu Pro Gly Ile
            610                 615                 620
Asn Tyr Ser Met Asp Glu Gln Cys Arg Phe Asp Phe Gly Ser Gly Tyr
625                 630                 635                 640
Gln Thr Cys Leu Ala Phe Arg Thr Phe Glu Pro Cys Lys Gln Leu Trp
            645                 650                 655
Cys Ser His Pro Asp Asn Pro Tyr Phe Cys Lys Thr Lys Lys Gly Pro
            660                 665                 670
Pro Leu Asp Gly Thr Glu Cys Ala Pro Gly Lys Trp Cys Phe Lys Gly
            675                 680                 685
His Cys Ile Trp Lys Ser Pro Glu Gln Thr Tyr Gly Gln Asp Gly Gly
            690                 695                 700
Trp Ser Ser Trp Thr Lys Phe Gly Ser Cys Ser Arg Ser Cys Gly Gly
705                 710                 715                 720
Gly Val Arg Ser Arg Ser Arg Ser Cys Asn Asn Pro Ser Pro Ala Tyr
            725                 730                 735
Gly Gly Arg Pro Cys Leu Gly Pro Met Phe Glu Tyr Gln Val Cys Asn
            740                 745                 750
Ser Glu Glu Cys Pro Gly Thr Tyr Glu Asp Phe Arg Ala Gln Gln Cys
            755                 760                 765
Ala Lys Arg Asn Ser Tyr Tyr Val His Gln Asn Ala Lys His Ser Trp
            770                 775                 780
Val Pro Tyr Glu Pro Asp Asp Ala Gln Lys Cys Glu Leu Ile Cys
785                 790                 795                 800
Gln Ser Ala Asp Thr Gly Asp Val Val Phe Met Asn Gln Val Val His
            805                 810                 815
```

-continued

```
Asp Gly Thr Arg Cys Ser Tyr Arg Asp Pro Tyr Ser Val Cys Ala Arg
            820                 825                 830

Gly Glu Cys Val Pro Val Gly Cys Asp Lys Glu Val Gly Ser Met Lys
            835                 840                 845

Ala Asp Asp Lys Cys Gly Val Cys Gly Gly Asp Asn Ser His Cys Arg
    850                 855                 860

Thr Val Lys Gly Thr Leu Gly Lys Ala Ser Lys Gln Ala Gly Ala Leu
865                 870                 875                 880

Lys Leu Val Gln Ile Pro Ala Gly Ala Arg His Ile Gln Ile Glu Ala
                885                 890                 895

Leu Glu Lys Ser Pro His Arg Ile Val Lys Asn Gln Val Thr Gly
            900                 905                 910

Ser Phe Ile Leu Asn Pro Lys Gly Lys Glu Ala Thr Ser Arg Thr Phe
    915                 920                 925

Thr Ala Met Gly Leu Glu Trp Glu Asp Ala Val Glu Asp Ala Lys Glu
    930                 935                 940

Ser Leu Lys Thr Ser Gly Pro Leu Pro Glu Ala Ile Ala Ile Leu Ala
945                 950                 955                 960

Leu Pro Pro Thr Glu Gly Gly Pro Arg Ser Leu Ala Tyr Lys Tyr
            965                 970                 975

Val Ile His Glu Asp Leu Leu Pro Leu Ile Gly Ser Asn Asn Val Leu
            980                 985                 990

Leu Glu Glu Met Asp Thr Tyr Glu Trp Ala Leu Lys Ser Trp Ala Pro
            995                 1000                1005

Cys Ser Lys Ala Cys Gly Gly Gly Ile Gln Phe Thr Lys Tyr Gly Cys
    1010                1015                1020

Arg Arg Arg Arg Asp His His Met Val Gln Arg His Leu Cys Asp His
1025                1030                1035                1040

Lys Lys Arg Pro Lys Pro Ile Arg Arg Arg Cys Asn Gln His Pro Cys
            1045                1050                1055

Ser Gln Pro Val Trp Val Thr Glu Glu Trp Gly Ala Cys Ser Arg Ser
            1060                1065                1070

Cys Gly Lys Leu Gly Val Gln Thr Arg Gly Ile Gln Cys Leu Met Pro
    1075                1080                1085

Leu Ser Asn Gly Thr His Lys Val Met Pro Ala Lys Ala Cys Ala Gly
    1090                1095                1100

Asp Arg Pro Glu Ala Arg Arg Pro Cys Leu Arg Val Pro Cys Pro Ala
1105                1110                1115                1120

Gln Trp Arg Leu Gly Ala Trp Ser Gln Cys Ser Ala Thr Cys Gly Glu
            1125                1130                1135

Gly Ile Gln Gln Arg Gln Val Val Cys Arg Thr Asn Ala Asn Ser Leu
            1140                1145                1150

Gly His Cys Glu Gly Asp Arg Pro Asp Thr Val Gln Val Cys Ser Leu
    1155                1160                1165

Pro Ala Cys Gly Gly Asn His Gln Asn Ser Thr Val Arg Ala Asp Val
    1170                1175                1180

Trp Glu Leu Gly Thr Pro Glu Gly Gln Trp Val Pro Gln Ser Glu Pro
1185                1190                1195                1200

Leu His Pro Ile Asn Lys Ile Ser Ser Thr Glu Pro Cys Thr Gly Asp
            1205                1210                1215

Arg Ser Val Phe Cys Gln Met Glu Val Leu Asp Arg Tyr Cys Ser Ile
            1220                1225                1230

Pro Gly Tyr His Arg Leu Cys Cys Val Ser Cys Ile Lys Lys Ala Ser
```

```
                 1235                 1240                 1245
Gly Pro Asn Pro Gly Pro Asp Pro Gly Pro Thr Ser Leu Pro Pro Phe
    1250                 1255                 1260
Ser Thr Pro Gly Ser Pro Leu Pro Gly Pro Gln Asp Pro Ala Asp Ala
1265                 1270                 1275                 1280
Ala Glu Pro Pro Gly Lys Pro Thr Gly Ser Glu Asp His Gln His Gly
                 1285                 1290                 1295
Arg Ala Thr Gln Leu Pro Gly Ala Leu Asp Thr Ser Ser Pro Gly Thr
        1300                 1305                 1310
Gln His Pro Phe Ala Pro Glu Thr Pro Ile Pro Gly Ala Ser Trp Ser
    1315                 1320                 1325
Ile Ser Pro Thr Thr Pro Gly Gly Leu Pro Trp Gly Trp Thr Gln Thr
        1330                 1335                 1340
Pro Thr Pro Val Pro Glu Asp Lys Gly Gln Pro Gly Glu Asp Leu Arg
1345                 1350                 1355                 1360
```

<210> SEQ ID NO 6
<211> LENGTH: 3699
<212> TYPE: DNA
<213> ORGANISM: Artificial Sequence
<220> FEATURE:
<223> OTHER INFORMATION: Description of Artificial Sequence: Synthetic
      EST 16 Genscan prediction sequence

<400> SEQUENCE: 6

```
atggctccac tccgcgcgct gctgtcctac ctgctgcctt tgcactgtgc gctctgcgcc    60
gccgcgggca gccggacccc agagctgcac ctctctggaa agctcagtga ctatggtgtg   120
acagtgccct gcagcacaga ctttcgggga cgcttcctct cccacgtggt gtctggccca   180
gcagcagcct ctgcagggag catggtagtg acacgccac ccacactacc acgacactcc    240
agtcacctcc gggtggctcg cagccctctg cacccaggag ggaccctgtg gcctggcagg   300
gtggggcgcc actccctcta cttcaatgtc actgttttcg ggaaggaact gcacttgcgc   360
ctgcggccca tcggaggtt ggtagtgcca ggatcctcag tggagtggca ggaggatttt    420
cgggagctgt tccggcagcc cttacggcag gagtgtgtgt acactggagg tgtcactgga   480
atgcctgggg cagctgttgc catcagcaac tgtgacggat ggcgggcct catccgcaca    540
gacagcaccg acttcttcat tgagcctctg agcggggcc agcaggagaa ggaggccagc    600
gggaggacac atgtggtgta ccgccgggag gccgtccagc aggagtgggc agaacctgac   660
ggggacctgc acaatgaagg agtttggctg tgggctgctg cgcttgccat tggctcagac   720
accagggcca ccagaagctg cctgcagtcc tttggcctgg agaccttcc caacctgctg    780
ggcctggtgg gggaccagct gggcgacaca gagcggaagc ggcggcatgc caagccaggc   840
agctacagca tcgaggtgct gctggtggtg gacgactcgg tggttcgctt ccatggcaag   900
gagcatgtgc agaactatgt cctcaccctc atgaatatcg tagatgagat ttaccacgat   960
gagtccctgg gggttcatat aaatattgcc ctcgtccgct tgatcatggt tggctaccga  1020
cagtccctga gcctgatcga gcgcgggaac ccctcacgca gcctggagca ggtgtgtcgc  1080
tgggcacact cccagcagcg ccaggacccc agccacgctg agcaccatga ccacgttgtg  1140
ttcctcaccc cgcaggactt tgggccctca gggtatgcac ccgtcactgg catgtgtcac  1200
cccctgagga gctgtgccct caaccatgag gatggcttct cctcagcctt cgtgatagct  1260
catgagaccg gccacgtgct cggcatggag catgacggtc aggggaatgg ctgtgcagat  1320
gagaccagcc tgggcagcgt catggcgccc ctggtgcagg ctgccttcca ccgcttccat  1380
```

-continued

```
tggtcccgct gcagcaagct ggagctcagc cgctacctcc cctcctacga ctgcctcctc    1440
gatgacccct ttgatcctgc ctggccccag cccccagagc tgcctgggat caactactca    1500
atggatgagc agtgccgctt tgactttggc agtggctacc agacctgctt ggcattcagg    1560
acctttgagc cctgcaagca gctgtggtgc agccatcctg acaacccgta cttctgcaag    1620
accaagaagg gcccccgct ggatgggact gagtgtgcac ccggcaagtg gtgcttcaaa     1680
ggtcactgca tctggaagtc gccggagcag acatatggcc aggatggagg ctggagctcc    1740
tggaccaagt ttgggtcatg ttcgcggtca tgtgggggcg gggtgcgatc ccgcagccgg    1800
agctgcaaca cccctcccc agcctatgga ggccgcccgt gcttagggcc catgttcgag     1860
taccaggtct gcaacagcga ggagtgccct gggacctacg aggacttccg ggcccagcag    1920
tgtgccaagc gcaactcgta ctatgtgcac cagaatgcca agcacagctg ggtgccctac    1980
gagcctgacg atgacgccca gaagtgtgag ctgatctgcc agtcggcgga cacgggggac    2040
gtggtgttca tgaaccaggt ggttcacgat gggacacgct gcagctaccg ggacccatac    2100
agcgtctgtg cgcgtggcga gtgtgtgcct gtcggctgtg acaaggaggt ggggtccatg    2160
aaggcggatg acaagtgtgg agtctgcggg ggtgacaact cccactgcag gactgtgaag    2220
gggacgctgg gcaaggcctc caagcaggca ggagctctca gctggtgca gatcccagca     2280
ggtgccaggc acatccagat tgaggcactg gagaagtccc cccaccgcat tgtggtgaag    2340
aaccaggtca ccggcagctt catcctcaac cccaagggca aggaagccac aagccggacc    2400
ttcaccgcca tgggcctgga gtgggaggat gcggtggagg atgccaagga aagcctcaag    2460
accagcgggc ccctgcctga agccattgcc atcctggctc tccccccaac tgagggtggc    2520
ccccgcagca gcctggccta caagtacgtc atccatgagg acctgctgcc ccttatcggg    2580
agcaacaatg tgctcctgga ggagatggac acctatgagt gggcgctcaa gagctgggcc    2640
ccctgcagca aggcctgtgg aggagggatc cagttcacca aatacggctg ccggcgcaga    2700
cgagaccacc acatggtgca gcgacacctg tgtgaccaca agaagaggcc caagcccatc    2760
cgccggcgct gcaaccagca cccgtgctct cagcctgtgt gggtgacgga ggagtggggt    2820
gcctgcagcc ggagctgtgg gaagctgggg gtgcagacac gggggataca gtgcctgatg    2880
cccctctcca atggaaccca caaggtcatg ccggccaaag cctgtgccgg ggaccggcct    2940
gaggcccgac ggccctgtct ccgagtgccc tgcccagccc agtggaggct gggagcctgg    3000
tcccagtgct ctgccacctg tggagagggc atccagcagc ggcaggtggt gtgcaggacc    3060
aacgccaaca gcctcgggca ttgcgagggg gataggccag acactgtcca ggtctgcagc    3120
ctgcctgcct gtggaggaaa tcaccagaac tccacggtga gggccgatgt ctgggaactt    3180
gggacgccag aggggcagtg ggtgccacaa tctgaacccc tacatcccat taacaagata    3240
tcatcaacgg agccctgcac gggagacagg tctgtcttct gccagatgga agtgctcgat    3300
cgctactgct ccattcccgg ctaccaccgg ctctgctgtg tgtcctgcat caagaaggcc    3360
tcgggcccca cccctggccc agaccctggc ccaacctcac tgccccctt ctccactcct     3420
ggaagcccct taccaggacc ccaggaccct gcagatgctg cagagcctcc tggaaagcca    3480
acgggatcag aggaccatca gcatggccga gccacacagc tcccaggagc tctggataca    3540
agctccccag ggacccagca tccctttgcc cctgagacac caatccctgg agcatcctgg    3600
agcatctccc ctaccacccc cggggggctg ccttggggct ggactcagac acctacgcca    3660
gtccctgagg acaaagggca acctggagaa gacctgaga                          3699
```

```
<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Zinc
      binding signature region

<400> SEQUENCE: 7

Thr Ala Ala His Glu Leu Gly His Val Lys Phe
 1               5                  10

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 8
ctggaggaga tggacaccta tgagtg                                          26

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 9
aaatgggcgc ggccgcttat ctcaggtctt ctccaggttg ccctttg                   47

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 10
aaatgggcga attcccacca tggctccact ccgcgcgctg ctgtccta                  48

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 11
gtagctgcct ggcttggcat gccg                                            24

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 12
accagctggg cgacacagag cggaagc                                         27

<210> SEQ ID NO 13
<211> LENGTH: 26
<212> TYPE: DNA
<213> ORGANISM: Artificial Sequence
```

```
<220> FEATURE:
<223> OTHER INFORMATION: Description of Artificial Sequence: Primer

<400> SEQUENCE: 13
ccgtatttgg tgaactggat ccctcc                                          26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 14
ctacaagtac gtcatccatg aggacc                                          26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 15
aatgaagaag tcggtgctgt ctgtgc                                          26

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 16
agtgacacct ccagtgtaca cacact                                          26

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 17
gaaaatcctc ctgccactcc actgag                                          26

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
catgggcagc tcgag                                                      15

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
```

```
ctgcaggcga gcctgaattc ctcgagccat catg                                34
```

<210> SEQ ID NO 20
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
cgaggttaaa aaacgtctag gccccccgaa ccacggggac gtggttttcc tttgaaaaac    60
acgattgc                                                             68
```

<210> SEQ ID NO 21
<211> LENGTH: 3672
<212> TYPE: DNA
<213> ORGANISM: Artificial Sequence
<220> FEATURE:
<223> OTHER INFORMATION: Description of Artificial Sequence: Synthetic
      GI nucleotide sequence

<400> SEQUENCE: 21

```
atggctccac tccgcgcgct gctgtcctac ctgctgcctt tgcactgtgc gctctgcgcc    60
gccgcgggca gccggacccc agagctgcac ctctctggaa agctcagtga ctatggtgtg   120
acagtgccct gcagcacaga cttccgggga cgcttcctct cccacgtggt gtctggccca   180
gcagcagcct ctgcagggag catggtagtg gacacgccac ccacactacc acgacactcc   240
agtcacctcc gggtggctcg cagccctctg cacccaggag ggaccctgtg gcctggcagg   300
gtggggcgcc actccctcta cttcaatgtc actgttttcg ggaaggaact gcacttgcgc   360
ctgcggccca atcggaggtt ggtagtgcca ggatcctcag tggagtggca ggaggatttt   420
cgggagctgt tccggcagcc cttacggcag gagtgtgtgt acactggagg tgtcactgga   480
atgcctgggg cagctgttgc catcagcaac tgtgacggat ggcgggcct catccgcaca   540 gacagcaccg acttcttcat tgagcctctg agcggggcc agcaggagaa ggaggccagc   600
gggaggacac atgtggtgta ccgccgggag gccgtccagc aggagtgggc agaacctgac   660
ggggacctgc acaatgaagc ctttggcctg ggagaccttc ccaacctgct gggcctggtg   720
ggggaccagc tgggcgacac agagcggaag cggcggcatg ccaagccagg cagctacagc   780
atcgaggtgc tactggtggt ggacgactcg gtggttcgct tccatggcaa ggagcatgtg   840
cagaactatg tcctcaccct catgaatatc gtagatgaga tttaccacga tgagtccctg   900
ggggttcata taaatattgc cctcgtccgc ttgatcatgg ttggctaccg acagtccctg   960
agcctgatcg agcgcgggaa ccctcacgc agcctggagc aggtgtgtcg ctgggcacac  1020
tcccagcagc gccaggaccc cagccacgct gagcaccatg accacgttgt gttcctcacc  1080
cggcaggact ttgggccctc agggtatgca cccgtcactg gcatgtgtca cccctgagg   1140 agctgtgccc tcaaccatga ggatggcttc tcctcagcct cgtgatagc tcatgagacc   1200 ggccacgtgc tcggcatgga gcatgacggt caggggaatg gctgtgcaga tgagaccagc  1260
ctgggcagcg tcatggcgcc cctggtgcag gctgccttcc accgcttcca ttggtcccgc  1320
tgcagcaagc tggagctcag ccgctacctc ccctcctacg actgcctcct cgatgacccc  1380
tttgatcctg cctggcccca gccccagag ctgcctggga tcaactactc aatggatgag  1440
cagtgccgct ttgactttgg cagtggctac cagacctgct ggcatttag gacctttgag  1500 ccctgcaagc agctgtggtg cagccatcct gacaacccgt acttctgcaa gaccaagaag  1560
```

```
gggcccccgc tggatgggac tgagtgtgca cccggcaagt ggtgcttcaa aggtcactgc   1620
atctggaagt cgccggagca gacatatggc caggatggag gctggagctc ctggaccaag   1680
tttgggtcat gttcgcggtc atgtgggggc ggggtgcgat cccgcagccg agctgcaac    1740 aacccctccc cagcctatgg aggccgcccg tgcttagggc ccatgttcga gtaccaggtc   1800
tgcaacagcg aggagtgccc tgggacctac gaggacttcc gggcccagca gtgtgccaag   1860
cgcaactcct actatgtgca ccagaatgcc aagcacagct gggtgcccta cgagcctgac   1920
gatgacgccc agaagtgtga gctgatctgc cagtcggcgg acacggggga cgtggtgttc   1980
atgaaccagg tggttcacga tgggacacgc tgcagctacc gggacccata cagcgtctgt   2040
gcgcgtggcg agtgtgtgcc tgtcggctgt gacaaggagg tggggtccat gaaggcggat   2100
gacaagtgtg gagtctgcgg gggtgacaac tcccactgca ggactgtgaa ggggacgctg   2160
ggcaaggcct ccaagcaggc aggagctctc aagctggtgc agatcccagc aggtgccagg   2220
cacatccaga ttgaggcact ggagaagtcc ccccaccgca ttgtggtgaa gaaccaggtc   2280
accggcagct tcatcctcaa ccccaagggc aaggaagcca caagccggac cttcaccgcc   2340
atgggcctgg agtgggagga tgcggtggag gatgccaagg aaagcctcaa gaccagcggg   2400
cccctgcctg aagccattgc catcctggct ctcccccccaa ctgagggtgg ccccccgcagc   2460 agcctggcct acaagtacgt catccatgag gacctgctgc cccttatcgg gagcaacaat   2520
gtgctcctgg aggagatgga cacctatgag tgggcgctca gagctgggc ccctgcagc    2580 aaggcctgtg gaggagggat ccagttcacc aaatacggct gccggcgcag acgagaccac   2640
cacatggtgc agcgacacct gtgtgaccac aagaagaggc caagcccat ccgccggcgc    2700 tgcaaccagc accgtgctc tcagcctgtg tgggtgacgg aggagtgggg tgcctgcagc   2760
cggagctgtg ggaagctggg ggtgcagaca cggggggatac agtgcctgat gcccctctcc   2820
aatggaaccc acaaggtcat gccggccaaa gcctgtgccg ggaccggcc tgaggcccga    2880 cggccctgtc tccgagtgcc ctgcccagcc cagtggaggc tgggagcctg gtcccagtgc   2940
tctgccacct gtggagaggg catccagcag cggcaggtgg tgtgcaggac caacgccaac   3000
agcctcgggc attgcgaggg ggataggcca gacactgtcc aggtctgcag cctgcctgcc   3060
tgtggaggaa atcaccagaa ctccacggtg agggccgatg tctgggaact tgggacgcca   3120
gaggggcagt gggtgccaca atctgaaccc ctacatccca ttaacaagat atcatcaacg   3180
gagccctgca cggagacag tctgtcttc tgccagatgg aggtgctcga tcgctactgc     3240
tccattcccg gctaccaccg gctctgctgt gtgtcctgca tcaagaaggc ctcgggcccc   3300
aaccctggcc cagaccctgg cccaacctca ctgccccct tctccactcc tggaagcccc    3360
ttaccaggac cccaggaccc tgcagatgct gcggagcctc ctggaaagcc aacgggatca   3420
gaggaccatc agcatggccg agccacacag ctcccaggag ctctggatac aagctcccca   3480
gggacccagc atccctttgc ccctgagaca ccaatccctg gagcatcctg gagcatctcc   3540
cctaccaccc ccgggggget gccttgggac tggactcaga cacctacgcc agtccctgag    3600
gacaaagggc aacctggaga agacctgaga catcccggca ccagcctccc tgctgcctcc   3660
ccggtgacat ga                                                       3672
```

AGGRECANASE MOLECULES

RELATED APPLICATION

This application relies on the benefit of priority to U.S. provisional patent application Nos. 60/308,386, filed on Jul. 27, 2001, and 60/315,887, filed on Aug. 29, 2001.

FIELD OF INVENTION

The present invention relates to the discovery of nucleotide sequences encoding novel aggrecanase molecules, the aggrecanase proteins and processes for producing them. The invention further relates to the development of inhibitors of, as well as antibodies to, the aggrecanase enzymes. These inhibitors and antibodies may be useful for the treatment of various aggrecanase-associated conditions including osteoarthritis.

BACKGROUND OF THE INVENTION

Aggrecan is a major extracellular component of articular cartilage. It is a proteoglycan responsible for providing cartilage with its mechanical properties of compressibility and elasticity. The loss of aggrecan has been implicated in the degradation of articular cartilage in arthritic diseases. Osteoarthritis is a debilitating disease which affects at least 30 million Americans (MacLean et al., *J Rheumatol* 25:2213–8 (1998)). Osteoarthritis can severely reduce quality of life due to degradation of articular cartilage and the resulting chronic pain. An early and important characteristic of the osteoarthritic process is loss of aggrecan from the HENDERSON extracellular matrix (Brandt and Mankin, "Pathogenesis of Osteoarthritis," *Textbook of Rheumatology*, WB Saunders Company, Philadelphia, Pa., at 1355–1373 (1993)). The large, sugar-containing portion of aggrecan is thereby lost from the extra-cellular matrix, resulting in deficiencies in the biomechanical characteristics of the cartilage.

A proteolytic activity termed "aggrecanase" is thought to be responsible for the cleavage of aggrecan thereby having a role in cartilage degradation associated with osteoarthritis and inflammatory joint disease. Work has been conducted to identify the enzyme responsible for the degradation of aggrecan in human osteoarthritic cartilage. Two enzymatic cleavage sites have been identified within the interglobular domain of aggrecan. One ($Asn^{34}$-$Phe^{342}$) is observed to be cleaved by several known metalloproteases. Flannery et al., *J Biol Chem*, 267:1008–14 (1992); Fosang et al., *Biochemical J.*, 304:347–351 (1994). The aggrecan fragment found in human synovial fluid, and generated by IL-1 induced cartilage aggrecan cleavage is at the $Glu^{373}$-$Ala^{374}$ bond (Sandy, et al., *J Clin Invest*, 69:1512–1516 (1992); Lohmander et al., *Arthritis Rheum* 36:1214–1222 (1993); Sandy et al., *J Biol Chem.*, 266:8683–8685 (1991)), indicating that none of the known enzymes are responsible for aggrecan cleavage in vivo.

Recently, identification of two enzymes, aggrecanase-1 (ADAMTS 4) and aggrecanase-2 (ADAMTS-11) within the "Disintegrin-like and Metalloprotease with Thrombospondin type 1 motif" (ADAM-TS) family have been identified which are synthesized by IL-1 stimulated cartilage and cleave aggrecan at the appropriate site (Tortorella, et al., *Science*, 284:1664–6 (1999); Abbaszade et al., *J Biol Chem*, 274: 23443–23450 (1999)). It is possible that these enzymes could be synthesized by osteoarthritic human articular cartilage. It is also contemplated that there are other, related enzymes in the ADAM-TS family which are capable of cleaving aggrecan at the $Glu^{373}$-$Ala^{374}$ bond and could contribute to aggrecan cleavage in osteoarthritis. There is a need to identify other aggrecanase enzymes and determine ways to block their activity.

SUMMARY OF THE INVENTION

The present invention is directed to the identification of aggrecanase protein molecules capable of cleaving aggrecan, the nucleotide sequences which encode the aggrecanase enzymes, and processes for the production of aggrecanases. These enzymes are contemplated to be characterized as having proteolytic aggrecanase activity. The invention further includes compositions comprising these enzymes.

The invention also includes antibodies to these enzymes, in one embodiment, for example, antibodies that block aggrecanase activity. In addition, the invention includes methods for developing inhibitors of aggrecanase which block the enzyme's proteolytic activity. These inhibitors and antibodies may be used in various assays and therapies for treatment of conditions characterized by the degradation of articular cartilage.

The invention provides an isolated DNA molecule comprising a DNA sequence chosen from: the sequence of SEQ ID NO: 1 from nucleotide #1–#4080; SEQ ID NO: 3 from nucleotide #1–#3691; and naturally occurring human allelic sequences and equivalent degenerative codon sequences.

The invention also comprises a purified aggrecanase protein comprising an amino acid sequence chosen from: the amino acid sequence set forth in SEQ ID NO: 5 from amino acid #1–#1360; SEQ ID NO: 4 from amino acid #1–#1223; and homologous aggrecanase proteins consisting of addition, substitution, and deletion mutants of the sequences.

The invention also provides a method of producing a purified aggrecanase protein.

The human aggrecanase protein or a fragment thereof may be produced by the steps of culturing a host cell transformed with a DNA molecule according to the invention, and recovering and purifying from the culture medium a protein comprising the amino acid sequence set forth in SEQ ID NOS: 4 or 5.

The invention also provides an antibody that binds to a purified aggrecanase protein of the invention. It also provides a method for developing inhibitors of aggrecanase comprising the use of an aggrecanase protein chosen from SEQ ID NOS: 4, 5, and a fragment thereof.

Additionally, it provides a pharmaceutical composition for inhibiting the proteolytic activity of aggrecanase, wherein the composition comprises at least one antibody according to the invention and at least one pharmaceutical carrier. It also provides a method for inhibiting aggrecanase in a mammal comprising administering to said mammal an effective amount of the pharmaceutical composition and allowing the composition to inhibit aggrecanase activity.

BRIEF DESCRIPTION OF THE SEQUENCES

This table summarizes information on the sequence listings provided in this application

| SEQUENCES | DESCRIPTION |
| --- | --- |
| 1 | Genscan predicted EST-16 |
| 2 | a.a. seq. of Genscan predicted EST-16 |

-continued

| SEQUENCES | DESCRIPTION |
|---|---|
| 3 | full-length confirmed EST16 |
| 4 | a.a. seq. of SEQ ID NO. 3 |
| 5 | a.a. seq. of Genscan 2 nucleotide sequence |
| 6 | synthetic EST-16 Genscan predicted sequence |
| 7 | sa. seq. - zinc binding signature region |
| 8 | nucleotide primer |
| 9 | nucleotide primer |
| 10 | nucleotide primer |
| 11 | nucleotide primer |
| 12 | nucleotide primer |
| 13 | nucleotide primer |
| 14 | nucleotide primer |
| 15 | nucleotide primer |
| 16 | nucleotide primer |
| 17 | nucleotide primer |
| 18 | synthetic oligonucleotide |
| 19 | synthetic oligonucleotide |
| 20 | synthetic oligonucleotide |
| 21 | synthetic EST-16 predicted nucleotides sequence | a.a. = amino acid

DETAILED DESCRIPTION OF THE INVENTION

I. Novel Aggrecanase Proteins

In one embodiment, the nucleotide sequence of an aggrecanase molecule of the present invention is chosen from SEQ ID NO: 1 from nucleotides #1–#4080, and SEQ ID NO: 3 from nucleotides #1–#3691. The invention further includes equivalent degenerative codon sequences of the sequences set forth in SEQ ID NOS: 1 and 3 as well as fragments thereof which exhibit aggrecanase activity. The full length sequence of the aggrecanase of the present invention may be obtained using the sequences of SEQ ID NOS: 1 or 3 to design probes for screening for the full sequence using standard techniques.

The amino acid sequence of the isolated aggrecanase-like molecule is set forth in SEQ ID NO: 5, as amino acids #1–#1360, and SEQ ID NO: 4, as amino acids #1–#1223. The invention further includes fragments of the amino acid sequences which encode molecules exhibiting aggrecanase activity.

The invention includes methods for obtaining the full length aggrecanase molecule, the DNA sequence obtained by this method and the protein encoded thereby. The method for isolation of the full length sequence involves utilizing the aggrecanase sequence set forth in SEQ ID NO: 1 or SEQ ID NO: 3 to design probes for screening, or otherwise screen, using standard procedures known to those skilled in the art.

The aggrecanase protein or a fragment thereof may be produced by culturing a cell transformed with the DNA sequence of SEQ ID NO: 1 comprising nucleotide #1–#4080 or SEQ ID NO: 3 comprising nucleotide #1–#3691 and recovering and purifying from the culture medium a protein characterized by the amino acid sequence set forth in SEQ ID NOS: 4 or 5. The purified expressed protein is substantially free from other proteinaceous materials with which it is co-produced, as well as from other contaminants. For production in mammalian cells, the DNA sequence further comprises a DNA sequence encoding a suitable propeptide 5' to and linked in frame to the nucleotide sequence encoding the aggrecanase enzyme.

The human aggrecanase proteins produced by the method discussed above are characterized by having the ability to cleave aggrecan and having an amino acid sequence chosen from SEQ ID NOS: 4 or 5 variants of the amino acid sequence of SEQ ID NOS: 4 or 5 including naturally occurring allelic variants, and other variants in which the proteins retain the ability to cleave aggrecan characteristic of aggrecanase proteins. Preferred proteins include a protein which is at least about 80% homologous, and more preferably at least about 90% homologous, to the amino acid sequence shown in SEQ ID NOS: 4 or 5. Finally, allelic or other variations of the sequences of SEQ ID NOS: 4 or 5 whether such amino acid changes are induced by mutagenesis, chemical alteration, or by alteration of DNA sequence used to produce the protein, where the peptide sequence still has aggrecanase activity, are also included in the present invention. The present invention also includes fragments of the amino acid sequence of SEQ ID NOS: 4 or 5 which retain the activity of aggrecanase protein.

II. Identification of Homologous Aggrecanase Proteins and DNA Encoding Them

It is expected that additional human sequences and other species have DNA sequences homologous to human aggrecanase enzyme. The invention, therefore, includes methods for obtaining the DNA sequences encoding other aggrecanase proteins, the DNA sequences obtained by those methods, and the protein encoded by those DNA sequences. This method entails utilizing the nucleotide sequence of the invention or portions thereof to design probes to screen libraries for the corresponding gene from other species or coding sequences or fragments thereof from using standard techniques. Thus, the present invention may include DNA sequences from other species, which are homologous to the human aggrecanase protein and can be obtained using the human sequence. The present invention may also include functional fragments of the aggrecanase protein, and DNA sequences encoding such functional fragments, as well as functional fragments of other related proteins. The ability of such a fragment to function is determinable by assay of the protein in the biological assays described for the assay of the aggrecanase protein.

For example, SEQ ID NO. 3 was used in a query against the Genbank databases in a BLASTN 2.2.2 search. Several sequences were identified as similar to SEQ ID NO. 3, differing only by splicing, truncation, or incomplete sequence. These sequences are disclosed in the following patents: WO 02/24927, WO 02/16564, WO 01/83782, WO 01/98468, WO 02/10216, WO 01/59133, and WO 200175067-A2. Some accession numbers with homology to EST-16 include BF906533, AJ403134, BF906535, BF823025, and BF906528. It is believed that these sequences are all part of the same family of ADAMTS. The cloning of ADAMTS17 has been described in Cal, S., et al., *Gene*, 283 (1–2):49–62 (2002). See also, Colige et al., *Cloning and Characterization of ADAMTS-14, A Novel ADAMTS Displaying High Homology with ADAMTS-2 and ADAMTS-3, J. Biol. Chem.*, 277(8):5756–5766 (2002).

Some examples of homologous, non-human sequences include a mouse sequence (sp:P97857), a rat sequence (sp:Q9WUQ1), *Arabidopsis thaliana* (NP 193602.1), *Caenorhabditis elegans* (NP 501792.1), and *Drosophila melanogaster* (NP 524645.1). It is expected that these sequences, from non-human species, are homologous to human aggrecanase enzymes.

The aggrecanase proteins provided herein also include factors encoded by the sequences similar to those of SEQ ID NO: 1 or SEQ ID NO: 3, but into which modifications or deletions are naturally provided (e.g., allelic variations in the nucleotide sequence which may result in amino acid changes in the protein) or deliberately engineered. For example, synthetic proteins may wholly or partially duplicate continuous sequences of the amino acid residues of SEQ ID NOS: 4 or 5. These sequences, by virtue of sharing primary, secondary, or tertiary structural and conformational characteristics with aggrecanase proteins may possess biological properties in common therewith. It is known, for example that numerous conservative amino acid substitutions are possible without significantly modifying the structure and conformation of a protein, thus maintaining the biological properties as well. For example, it is recognized that conservative amino acid substitutions may be made among amino acids with basic side chains, such as lysine (Lys or K), arginine (Arg or R) and histidine (His or H); amino acids with acidic side chains, such as aspartic acid (Asp or D) and glutamic acid (Glu or E); amino acids with uncharged polar side chains, such as asparagine (Asn or N), glutamine (Gln or Q), serine (Ser or S), threonine (Thr or T), and tyrosine (Tyr or Y); and amino acids with nonpolar side chains, such as alanine (Ala or A), glycine (Gly or G), valine (Val or V), leucine (Leu or L), isoleucine (Ile or I), proline (Pro or P), phenylalanine (Phe or F), methionine (Met or M), tryptophan (Trp or W) and cysteine (Cys or C). Thus, these modifications and deletions of the native aggrecanase may be employed as biologically active substitutes for naturally-occurring aggrecanase and in the development of inhibitors or other proteins in therapeutic processes. It can be readily determined whether a given variant of aggrecanase maintains the biological activity of aggrecanase by subjecting both aggrecanase and the variant of aggrecanase, as well as inhibitors thereof, to the assays described in the examples.

Other specific mutations of the sequences of aggrecanase proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of aggrecanase-related protein will also result in production of a non-glycosylated protein, even if the glycosylation sites are left unmodified.

III. Novel Aggrecanase Nucleotide Sequences

Still a further aspect of the invention are DNA sequences coding for expression of an aggrecanase protein having aggrecanase proteolytic activity or other disclosed activities of aggrecanase. Such sequences include the sequence of nucleotide in a 5' to 3' direction set forth in SEQ ID NO: 1 or SEQ ID NO: 3 and DNA sequences which, but for the degeneracy of the genetic code, are identical to the DNA sequence of SEQ ID NO: 1 or SEQ ID NO: 3, and encode an aggrecanase protein.

Further included in the present invention are DNA sequences which hybridize under stringent conditions with the DNA sequence of SEQ ID NO: 1 or SEQ ID NO: 3 and encode a protein having the ability to cleave aggrecan. Preferred DNA sequences include those which hybridize under stringent conditions (see, T. Maniatis et al., *Molecular Cloning* (*A Laboratory Manual*), Cold Spring Harbor Laboratory at 387–389 (1982). Such stringent conditions comprise, for example, 0.1×SSC, 0.1% SDS, at 65° C.

Similarly, DNA sequences which code for aggrecanase proteins coded for by the sequences of SEQ ID NO: 1 or SEQ ID NO: 3, or aggrecanase proteins which comprise the amino acid sequences of SEQ ID NO: 4 or 5, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO: 1 or SEQ ID NO: 3 which are caused by point mutations or by induced modifications (including insertion, HENDERSON deletion, and substitution) to enhance the activity, half-life or production of the proteins encoded are also encompassed in the invention.

The DNA sequences of the present invention are useful, for example, as probes for the detection of mRNA encoding aggrecanase in a given cell population. Thus, the present invention includes methods of detecting or diagnosing genetic disorders involving the aggrecanase, or disorders involving cellular, organ or tissue disorders in which aggrecanase is irregularly transcribed or expressed. Antisense DNA sequences may also be useful for preparing vectors for gene therapy applications. Antisense DNA sequences are also useful for in vivo methods, such as to introduce the antisense DNA into the cell, to study the interaction of the antisense DNA with the native sequences, and to test the capacity of a promoter operatively linked to the antisense DNA in a vector by studying the interaction of antisense DNA in the cell as a measure of how much antisense DNA was produced.

A further aspect of the invention includes vectors comprising a DNA sequence as described above in operative association with an expression control sequence therefor. These vectors may be employed in a novel process for producing an aggrecanase protein of the invention in which a cell line transformed with a DNA sequence encoding an aggrecanase protein in operative association with an expression control sequence therefor, is cultured in a suitable culture medium and an aggrecanase protein is recovered and purified therefrom. This process may employ a number of known cells both prokaryotic and eukaryotic as host cells for expression of the polypeptide. The vectors may be used in gene therapy applications. In such use, the vectors may be transfected into the cells of a patient ex vivo, and the cells may be reintroduced into a patient. Alternatively, the vectors may be introduced into a patient in vivo through targeted transfection.

The construction of vectors may involve modification of the aggrecanase-related DNA sequences. For instance, aggrecanase cDNA can be modified by removing the non-coding nucleotide on the 5' and 3' ends of the coding region. The deleted non-coding nucleotide may or may not be replaced by other sequences known to be beneficial for expression. These vectors are transformed into appropriate host cells for expression of aggrecanase-related proteins. Additionally, the sequence of SEQ ID NO: 1, SEQ ID NO: 3 or other sequences encoding aggrecanase-related proteins can be manipulated to express a mature aggrecanase-related protein by deleting aggrecanase encoding propeptide sequences and replacing them with sequences encoding the complete propeptides of other aggrecanase proteins.

One skilled in the art can manipulate the sequences of SEQ ID NO: 1 or SEQ ID NO: 3 by eliminating or replacing the mammalian regulatory sequences flanking the coding sequence with bacterial sequences to create bacterial vectors for intracellular or extracellular expression by bacterial cells. For example, the coding sequences could be further manipulated (e.g., ligated to other known linkers or modified by deleting non-coding sequences therefrom or altering nucleotide therein by other known techniques). The modified aggrecanase-related coding sequence could then be inserted into a known bacterial vector using procedures such as described in Taniguchi et al., *Proc. Natl Acad. Sci. USA,* 77:5230–5233 (1980). This exemplary bacterial vector could then be transformed into bacterial host cells and an aggrecanase-related protein expressed thereby. For a strategy for producing extracellular expression of aggrecanase-related proteins in bacterial cells, see, e.g. European patent application EPA 177,343.

Similar manipulations can be performed for the construction of an insect vector (See, e.g., procedures described in published European patent application 155,476) for expression in insect cells. A yeast vector could also be constructed employing yeast regulatory sequences for intracellular or extracellular expression of the factors of the present invention by yeast cells. (See, e.g., procedures described in published PCT application WO86/00639 and European patent application EPA 123,289).

A method for producing high levels of an aggrecanase-related protein of the invention in mammalian, bacterial, yeast or insect host cell systems may involve the construction of cells containing multiple copies of the heterologous aggrecanase-related gene. The heterologous gene is linked to an amplifiable marker, e.g., the dihydrofolate reductase (DHFR) gene for which cells containing increased gene copies can be selected for propagation in increasing concentrations of methotrexate (MTX) according to the procedures of Kaufman and Sharp, *J. Mol. Biol.,* 159:601–629 (1982). This approach can be employed with a number of different cell types.

For example, a plasmid containing a DNA sequence for an aggrecanase-related protein of the invention in operative association with other plasmid sequences enabling expression thereof and the DHFR expression plasmid pAdA26SV (A)3 (Kaufman and Sharp, *Mol. Cell. Biol.,* 2:1304 (1982)) can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 uM MTX) as described in Kaufman et al., *Mol Cell Biol.,* 5:1750 (1983). Transformants are cloned, and biologically active aggrecanase expression is monitored by the assays described above. Aggrecanase protein expression should increase with increasing levels of MTX resistance. Aggrecanase proteins are characterized using standard techniques known in the art such as pulse labeling with $^{35}$S methionine or cysteine and polyacrylamide gel electrophoresis. Similar procedures can be followed to produce other related aggrecanase-related proteins.

IV. Production of Aggrecanase Proteins

Another aspect of the present invention provides a novel method for producing novel aggrecanase proteins. The method of the present invention involves culturing a suitable cell line, which has been transformed with a DNA sequence encoding an aggrecanase protein of the invention, under the control of known regulatory sequences. The transformed host cells are cultured and the aggrecanase proteins recovered and purified from the culture medium. The purified proteins are substantially free from other proteins with which they are co-produced as well as from other contaminants. The recovered purified protein is contemplated to exhibit proteolytic aggrecanase activity cleaving aggrecan. Thus, the proteins of the invention may be further characterized by the ability to demonstrate aggrecan proteolytic activity in an assay which determines the presence of an aggrecan-degrading molecule. These assays or the development thereof is within the knowledge of one skilled in the art. Such assays may involve contacting an aggrecan molecule and monitoring the production of aggrecan fragments (see for example, Hughes et al., *Biochem J,* 305:799–804 (1995); Mercuri et al., *J. Bio Chem.,* 274:32387–32395 (1999)).

Suitable cells or cell lines may be mammalian cells, such as Chinese hamster ovary cells (CHO). The selection of suitable mammalian host cells and methods for transformation, culture, amplification, screening, product production and purification are known in the art. (See, e.g., Gething and Sambrook, *Nature,* 293:620–625 (1981), Kaufman et al., *Mol. Cell. Biol.,* 5(7):1750–1759 (1985); Howley et al., U.S. Pat. No. 4,419,446.) Another suitable mammalian cell line, which is described in the accompanying examples, is the monkey COS-1 cell line. The mammalian cell CV-1 may also be suitable.

Bacterial cells may also be suitable hosts. For example, the various strains of *E. coil* (e.g., HB101, MC1061) are well-known as host cells in the field of biotechnology. Various strains of *B. subtilis, Pseudomonas,* other *bacilli* and the like may also be employed in this method. For expression of the protein in bacterial cells, DNA encoding the propeptide of aggrecanase is generally not necessary.

Many strains of yeast cells known to those skilled in the art may also be available as host cells for expression of the polypeptides of the present invention. Additionally, where desired, insect cells may be utilized as host cells in the method of the present invention. See, e.g. Miller et al., *Genetic Engineering,* 8:277–298 (Plenum Press 1986).

Another aspect of the present invention provides vectors for use in the method of expression of these novel aggrecanase polypeptides. Preferably the vectors contain the full novel DNA sequences described above which encode the novel factors of the invention. Additionally, the vectors contain appropriate expression control sequences permitting expression of the aggrecanase protein sequences. Alternatively, vectors incorporating modified sequences as described above are also embodiments of the present invention. Additionally, the sequence of SEQ ID NO: 1, SEQ ID NO: 3 or other sequences encoding aggrecanase proteins could be manipulated to express composite aggrecanase proteins. Thus, the present invention includes chimeric DNA molecules encoding an aggrecanase protein comprising a fragment from SEQ ID NO: 1 or SEQ ID NO: 3 linked in correct reading frame to a DNA sequence encoding another aggrecanase protein.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

V. Generation of Antibodies

The purified proteins of the present inventions may be used to generate antibodies, either monoclonal or polyclonal, to aggrecanase and/or other aggrecanase-related proteins, using methods that are known in the art of antibody production. Thus, the present invention also includes antibodies to aggrecanase or other related proteins. The antibodies include both those that block aggrecanase activity and those that do not. The antibodies may be useful for detection and/or purification of aggrecanase or related proteins, or for inhibiting or preventing the effects of aggrecanase. The aggrecanase of the invention or portions thereof may be utilized to prepare antibodies that specifically bind to aggrecanase.

The term "antibody" as used herein, refers to an immunoglobulin or a part thereof, and encompasses any protein comprising an antigen binding site regardless of the source, method of production, and characteristics. The term includes but is not limited to polyclonal, monoclonal, monospecific, polyspecific, non-specific, humanized, single-chain, chimeric, synthetic, recombinant, hybrid, mutated, and DCR-grafted antibodies. It also includes, unless otherwise stated, antibody fragments such as Fab, F(ab')$_2$, Fv, scFv, Fd, dAb, and other antibody fragments which retain the antigen binding function.

Antibodies can be made, for example, via traditional hybridoma techniques (Kohler and Milstein, *Nature* 256: 495–499 (1975)), recombinant DNA methods (U.S. Pat. No. 4,816,567), or phage display techniques using antibody libraries (Clackson et al., *Nature* 352:624–628 (1991); Marks et al., *J. Mol. Biol.,* 222:581–597 (1991)). For various other antibody production techniques, see Antibodies: A Laboratory Manual, eds. Harlow et al., Cold Spring Harbor Laboratory (1988).

An antibody "specifically" binds to at least one novel aggrecanase molecule of the present invention when the antibody will not show any significant binding to molecules other than at least one novel aggrecanase molecule. The term is also applicable where, e.g., an antigen binding domain is specific for a particular epitope, which is carried by a number of antigens, in which case the specific binding member (the antibody) carrying the antigen binding domain will be able to bind to the various antigens carrying the epitope. In this fashion it is possible that an antibody of the invention will bind to multiple novel aggrecanase proteins. Typically, the binding is considered specific when the affinity constant $K_a$ is higher than $10^8$ $M^{-1}$. An antibody is said to "specifically bind" or "specifically react" to an antigen if, under appropriately selected conditions, such binding is not substantially inhibited, while at the same time non-specific binding is inhibited. Such conditions are well known in the art, and a skilled artisan using routine techniques can select appropriate conditions. The conditions are usually defined in terms of concentration of antibodies, ionic strength of the solution, temperature, time allowed for binding, concentration of non-related molecules (e.g., serum albumin, milk casein), etc.

Proteins are known to have certain biochemical properties including sections which are hydrophobic and sections which are hydrophilic. The hydrophobic sections would most likely be located in the interior of the structure of the protein while the hydrophilic sections would most likely be located in the exterior of the structure of the protein. It is believed that the hydrophilic regions of a protein would then correspond to antigenic regions on the protein. Knowing the location of the antigenic regions would enable one of ordinary skill in the art to then generate antibodies specific to that region. The hydrophobicity of SEQ ID NO. 3 was determined using GCG PepPlot. The results indicated that the n-terminus was hydrophobic presumably because of a signal sequence.

VI. Development of Inhibitors

Various conditions such as osteoarthritis are known to be characterized by degradation of aggrecan. Therefore, an aggrecanase protein of the present invention which cleaves aggrecan may be useful for the development of inhibitors of aggrecanase. The invention therefore provides compositions comprising an aggrecanase inhibitor. The inhibitors may be developed using the aggrecanase in screening assays involving a mixture of aggrecan substrate with the inhibitor followed by exposure to aggrecan. Inhibitors can be screened using high throughput processes, such as by screening a library of inhibitors. Inhibitors can also be made using three-dimensional structural analysis and/or computer aided drug design. The compositions may be used in the treatment of osteoarthritis and other conditions exhibiting degradation of aggrecan.

VII. Administration

Another aspect of the invention therefore provides pharmaceutical compositions containing a therapeutically effective amount of aggrecanase antibodies and/or inhibitors, in a pharmaceutically acceptable vehicle. Aggrecanase-mediated degradation of aggrecan in cartilage has been implicated in osteoarthritis and other inflammatory diseases. Therefore, these compositions of the invention may be used in the treatment of diseases characterized by the degradation of aggrecan and/or an up regulation of aggrecanase. The compositions may be used in the treatment of these conditions or in the prevention thereof.

The invention includes methods for treating patients suffering from conditions characterized by a degradation of aggrecan or preventing such conditions. These methods, according to the invention, entail administering to a patient needing such treatment, an effective amount of a composition comprising an aggrecanase antibody or inhibitor which inhibits the proteolytic activity of aggrecanase enzymes.

The antibodies and inhibitors of the present invention are useful to prevent, diagnose, or treat various medical disorders in humans or animals. In one embodiment, the antibodies can be used to inhibit or reduce one or more activities associated with the aggrecanase protein, relative to an aggrecanase protein not bound by the same antibody. Most preferably, the antibodies and inhibitors inhibit or reduce one or more of the activities of aggrecanase relative to the aggrecanase that is not bound by an antibody. In certain embodiments, the activity of aggrecanase, when bound by one or more of the presently disclosed antibodies, is inhibited at least 50%, preferably at least 60, 62, 64, 66, 68, 70, 72, 72, 76, 78, 80, 82, 84, 86, or 88%, more preferably at least 90, 91, 92, 93, or 94%, and even more preferably at least 95% to 100% relative to an aggrecanase protein that is not bound by one or more of the presently disclosed antibodies.

Generally, the compositions are administered so that antibodies/their binding fragments are given at a dose between 1 µg/kg and 20 mg/kg, 1 µg/kg and 10 mg/kg, 1 µg/kg and 1 mg/kg, 10 µg/kg and 1 mg/kg, 10 µg/kg and 100 µg/kg, 100 µg and 1 mg/kg, and 500 µg/kg and 1 mg/kg. Preferably, the antibodies are given as a bolus dose, to maximize the circulating levels of antibodies for the greatest length of time after the dose. Continuous infusion may also be used after the bolus does.

In another embodiment and for administration of inhibitors, such as proteins and small molecules, an effective amount of the inhibitor is a dosage which is useful to reduce the activity of aggrecanase to achieve a desired biological outcome. Generally, appropriate therapeutic dosages for administering an inhibitor may range from 5 mg to 100 mg, from 15 mg to 85 mg, from 30 mg to 70 mg, or from 40 mg to 60 mg. Inhibitors can be administered in one dose, or at intervals such as once daily, once weekly, and once monthly. Dosage schedules can be adjusted depending on the affinity for the inhibitor to the aggrecanase target, the half-life of the inhibitor, and the severity of the patient's condition. Generally, inhibitors are administered as a bolus dose, to maximize the circulating levels of inhibitor. Continuous infusions may also be used after the bolus dose.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antibodies and inhibitors, which exhibit large therapeutic indices, are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any antibody and inhibitor used in the present invention, the therapeutically effective dose can be estimated initially from cell culture assays. A dose may be formulated in animal models to achieve a circulating plasma concentration range that includes the $IC_{50}$ (i.e., the concentration of the test antibody which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include DNA replication assays, transcription-based assays, GDF protein/receptor binding assays, creatine kinase assays, assays based on the differentiation of pre-adipocytes, assays based on glucose uptake in adipocytes, and immunological assays.

The therapeutic methods of the invention include administering the aggrecanase inhibitor compositions topically, systemically, or locally as an implant or device. The dosage regimen will be determined by the attending physician considering various factors which modify the action of the aggrecanase protein, the site of pathology, the severity of disease, the patient's age, sex, and diet, the severity of any inflammation, time of administration and other clinical factors. Generally, systemic or injectable administration will be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known factors, to the final composition, may also effect the dosage.

Progress can be monitored by periodic assessment of disease progression. The progress can be monitored, for example, by x-rays, MRI or other imaging modalities, synovial fluid analysis, and/or clinical examination.

VIII. Assays and Methods of Detection

The inhibitors and antibodies of the invention can be used in assays and methods of detection to determine the presence or absence of, or quantify aggrecanase in a sample. The inhibitors and antibodies of the present invention may be used to detect aggrecanase proteins, in vivo or in vitro. By correlating the presence or level of these proteins with a medical condition, one of skill in the art can diagnose the associated medical condition or determine its severity. The medical conditions that may be diagnosed by the presently disclosed inhibitors and antibodies are set forth above.

Such detection methods for use with antibodies are well known in the art and include ELISA, radioimmunoassay, immunoblot, western blot, immunofluorescence, immunoprecipitation, and other comparable techniques. The antibodies may further be provided in a diagnostic kit that incorporates one or more of these techniques to detect a protein (e.g., an aggrecanase protein). Such a kit may contain other components, packaging, instructions, or other material to aid the detection of the protein and use of the kit. When protein inhibitors are used in such assays, protein-protein interaction assays can be used.

Where the antibodies and inhibitors are intended for diagnostic purposes, it may be desirable to modify them, for example, with a ligand group (such as biotin) or a detectable marker group (such as a fluorescent group, a radioisotope or an enzyme). If desired, the antibodies (whether polyclonal or monoclonal) may be labeled using conventional techniques. Suitable labels include fluorophores, chromophores, radioactive atoms, electron-dense reagents, enzymes, and ligands having specific binding partners. Enzymes are typically detected by their activity. For example, horseradish peroxidase can be detected by its ability to convert tetramethylbenzidine (TMB) to a blue pigment, quantifiable with a spectrophotometer. Other suitable binding partners include biotin and avidin or streptavidin, IgG and protein A, and the numerous receptor-ligand couples known in the art.

The following non-limiting examples illustrate practice of the present invention in isolating and characterizing human aggrecanase and other aggrecanase-related proteins, obtaining the human proteins and expressing the proteins via recombinant techniques.

EXAMPLES

Example 1

Isolation of DNA

Potential novel aggrecanase family members were identified using a database screening approach. Aggrecanase-1 (*Science*, 284:1664–1666 (1999)) has at least six domains: signal, propeptide, catalytic domain, disintegrin, tsp and c-terminal. The catalytic domain contains a zinc binding signature region, TAAHELGHVKF (SEQ ID NO: 7) and a "MET turn" which are responsible for protease activity. Substitutions within the zinc binding region in the number of the positions still allow protease activity, but the histidine (H) and glutamic acid (E) residues must be present. The thrombospondin domain of Aggrecanase-1 is also a critical domain for substrate recognition and cleavage. It is these two domains that determine our classification of a novel aggrecanase family member. The protein sequence of the Aggrecanase-1 DNA sequence was used to query against the GenBank ESTs focusing on human ESTs using TBLASTN. The resulting sequence Genbank EST AJ403134 was the starting point in the effort to identify a full length sequence for potential family members. The nucleotide sequence of the aggrecanase of the present invention is comprised of one EST, EST-16, that contains homology over the catalytic domain and zinc binding motif of Aggrecanase-1. The structure of the entire gene was reconstructed using public DNA sequences and a Genscan prediction of the gene found in the Celera Genome Browser (Rockville, Md., USA).

The human aggrecanase gene was isolated using a PCR strategy with tissue sources determined by probing a Clontech Human Multiple Tissue Expression Array (MTE) (Palo Alto, Calif., USA). The probe for the MTE was generated using PCR primers that amplified the 3' end of the EST-16 Genscan predicted sequence, SEQ ID NO: 1 from bp 2977–4080. Primer sequences were as follows: 5' primer sequence—CTGGAGGAGATGGACACCTATGAGTG (SEQ ID NO: 8) and 3' primer sequence—AAATGGGCGCGGCCGCTTATCTCAG-GTCTTCTCCAGGTTGCCCTTTG (SEQ ID NO: 9) (this primer incorporated a stop codon (TAA), a Not 1 sequence (GCGGCCGC) and an 8 bp tail (GCCCATTT) onto the end of the EST-16 Genscan predicted sequence). A Wyeth human uterus oligo dT-primed cDNA library (FL60) was used as substrate with the PCR primer set to amplify the appropriate 1103 bp EST-16 fragment (SEQ ID NO: 1, bp 2977–4080). The Advantage-GC 2 PCR Kit from Clontech was used for the PCR reactions. Reaction conditions were those recommended in the user manual; with the following exceptions: the amount of GC Melt used was 5 µl per 50 µl reaction; the amount of non-linearized library used was 1 ng/µl reaction; and the amount of each oligo used was 0.1 pmol/µl reaction. Cycling conditions were as follows: 94° C. for 1 min, one cycle; followed by 40 cycles consisting of 95° C. for 15 sec/68° C. for 3 min. The PCR fragment representing the 3' end of EST-16 was radiolabelled using the Ready-To-Go DNA Labelling Beads (-dCTP) from Amersham Pharmacia Biotech (Piscataway, N.J., USA) per the manufacturer's instructions. The radiolabelled fragment was purified away from primers and unincorporated radionucleotides using a Nick column from Amersham Pharmacia Biotech per the manufacturer's instructions and then used to probe the MTE. Manufacturer's conditions for hybridization of the MTE using a radiolabelled cDNA probe were followed. EST-16 was found to be expressed in a leukemia K-562 cell line, in an adenocarcinoma SW480 cell line and in fetal lung tissue. Marathon-Ready cDNAs corresponding to these cell lines or tissue were purchased from Clontech: human colorectal adenocarcinoma SW480 cell line, ATCC#CCL228; human fetal lung pooled from 9 male/female Caucasian fetuses, ages 20–25 weeks; and human leukemia, chronic myelogenous K-562 cell line, ATCC#CCL243. PCR primers to the 5' and internal portions of the EST-16 Genscan predicted sequence were designed. Three overlapping pieces of EST-16 were amplified using the following primer sets. The first PCR primer set amplified from bp 1–1227 of the EST-16 Genscan predicted sequence, SEQ ID NO: AAATGGGCG-MTTCCCACCATGGCTCCACTC-CGCGCGCTGCTGTCCTA (SEQ ID NO: 10) (this primer incorporated an 8 bp tail (AAATGGGC), an EcoR1 sequence (GAATTC) and a Kozak sequence (CCACC) upstream of the initiator Met (ATG)) and the 3' primer sequence—GTAGCTGCCTGGCTTGGCATGCCG (SEQ ID NO: 11). The second primer set amplified from bp 1175–3068 of the EST-16 Genscan predicted sequence, SEQ ID NO: 1; 5' primer sequence—ACCAGCTGGGCGACA-CAGAGCGGMGC (SEQ ID NO: 12) and the 3' primer sequence—CCGTATTTGGTGMCTGGATCCCTCC (SEQ ID NO: 13). The third PCR primer set amplified from bp 2977–4080 of the EST-16 Genscan predicted sequence; 5' primer sequence—CTGGAGGAGATGGACACCTAT-GAGTG (SEQ ID NO: 8) and 3' primer sequence—AAATGGGCGCGGCCGCTTATCTCAG-GTCTTCTCCAGGTTGCCCTTTG (SEQ ID NO: 9) (this primer incorporated a stop codon (TAA), a Not1 sequence (GCGGCCGC), and an 8 bp tail (GCCCATTT) onto the end of the EST-16 Genscan predicted sequence). The Advantage-GC 2 PCR Kit from Clontech was used to amplify the EST-16 gene products. Reaction conditions were those recommended in the user manual; with the following exceptions: the amount of GC Melt used was 5 µl per 50 µl reaction; the amount of Marathon cDNA used was 0.01 ng/µl of reaction; and the amount of each oligo used was 0.1 pmol/µl. Cycling conditions were as follows: 94° C. for 1 min, one cycle; followed by 40 cycles consisting of 95° C. for 15 sec/68° C. for 3 min. Each of the primer pairs were used in PCR amplification reactions containing each of the 3 Marathon cDNAs. PCR products resulting from the amplifications were ligated into the pT-Adv vector using the AdvanTAge PCR Cloning Kit, per manufacturer's instructions. Ligated products were transformed into ElectroMAX DH10B cells from Life Technologies (Carlsbad, Calif., USA). Cloned PCR fragments of EST-16 were sequenced to determine fidelity. PCR products with the correct sequence were moved from the pT-Adv vector into the Cos expression vector pED6-dpc2 and a full-length version of EST-16 was constructed as set forth in SEQ ID NO: 3. The full-length sequence for EST-16 was the consensus sequence derived from the EST-16 Genscan sequence and the PCR products generated for EST-16 from each of the 3 unique Clontech Marathon cDNAs. The 5' and 3' ends of EST-16 sequence were confirmed by RACE PCR using the Clontech Marathon cDNA Amplification Kit. The same Marathon cDNA sources used to PCR the EST-16 gene were the substrates for the RACE reactions. 3' RACE primers used were; GSP1—CTACAAGTACGTCATCCATGAGGACC (SEQ ID NO: 14) and GSP2—CTGGAGGAGATGGACACCTAT-GAGTG (SEQ ID NO: 8). Two sets of 5' RACE primers were used; the first set=GSP1—AATGAAGAAGTCGGT-GCTGTCTGTGC (SEQ ID NO: 15) and GSP2—AGTGA-CACCTCCAGTGTACACACACT (SEQ ID NO: 16). The second set=GSP1—AATGAAGAAGTCGGTGCTGTCT-GTGC (SEQ ID NO: 15) and GSP2—GAAAATCCTCCT-GCCACTCCACTGAG (SEQ ID NO: 17). The Advantage-GC2 PCR Kit from Clontech was used to set up nested RACE reactions following instructions in the user manual for the Marathon cDNA Amplification Kit; the amount of GC Melt used was 5 µl per 50 µl reaction, and the amount the GSP oligos used was 0.1 pmol/µl. In all cases GSP1 primers were used for the first round of PCR and GSP2 primers were used for the nested reactions. Information from the 5' RACE confirmed the EST-16 Genscan predicted initiator Met. Information from the 3' RACE revealed an error in the sequence used for the 3' end of EST-16. The sequence was repaired using synthetic oligos from bp 3585 to the end of the full-length EST-16 (bp 3683). The synthetic oligos inserted a Not1 sequence following the naturally occuring stop codon (TGA). This synthetic sequence reflected the stop predicted by a revised copy of the Genscan predicted sequence and confirmed by RACE PCR.

The nucleotide sequence is set forth in SEQ ID NO: 1 from nucleotide #1 to #4080. The full length confirmed sequence is set forth in SEQ ID NO: 3. The amino acid sequence is set forth in SEQ ID NO: 5 from amino acid #1–#1360. EST-16 sequence as set forth in SEQ ID NO: 3 has been deposited in the American Type Culture Collection 10801 University Blvd. Manassas, Va. 20110-2209 USA on May 30, 2001 as ATCC No. PTA 3410.

The aggrecanase nucleotide sequence of the invention can be used to design probes for further screening for full length clones containing the isolated sequence.

Example 2

Expression of Aggrecanase

In order to produce murine, human or other mammalian aggrecanase-related proteins, the DNA encoding it is transferred into an appropriate expression vector and introduced into mammalian cells or other preferred eukaryotic or prokaryotic hosts including insect host cell culture systems by conventional genetic engineering techniques. Expression system for biologically active recombinant human aggrecanase are contemplated to be stably transformed mammalian cells, insect, yeast or bacterial cells. Expression of aggrecan may be found in larynx carcinoma, kidney tumor, and ovary tissue.

One skilled in the art can construct mammalian expression vectors by employing a sequence comprising SEQ ID NOS: 1, 3, or other DNA sequences encoding aggrecanase-related proteins or other modified sequences and known vectors, such as pCD (Okayama et al., *Mol. Cell Biol.*, 2:161–170 (1982)), pJL3, pJL4 (Gough et al., *EMBO J.*, 4:645–653 (1985)) and pMT2 CXM.

The mammalian expression vector pMT2 CXM is a derivative of p91023(b) (Wong et al., *Science*, 228:810–815 (1985)) differing from the latter in that it contains the ampicillin resistance gene in place of the tetracycline resistance gene and further contains a XhoI site for insertion of cDNA clones. The functional elements of pMT2 CXM have been described (Kaufman, *Proc. Natl. Acad. Sci. USA*, 82:689–693 (1985)) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM is obtained by EcoR1 digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods. pMT2 CXM is then constructed using loopout/in mutagenesis (Morinaga, et al., *Biotechnology*, 84: 636 (1984)). This removes bases 1075 to 1145 relative to the Hind III site near the SV40 origin of replication and enhancer sequences of pMT2. In addition it inserts the following sequence: 5' PO-CATGGGCAGCTCGAG-3' (SEQ ID NO: 18) at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform *E. Coli* HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR: 5'—

```
                                      (SEQ ID NO:19)
    CTGCAGGCGAGCCTGAATTCCTCGAGCCATCATG-3'
    PstI            Eco RI   XhoI
```

Second, a unique ClaI site is introduced by digestion with EcoRV and XbaI, treatment with Klenow fragment of DNA polymerase 1, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 (S. K. Jung, et al., *J. Virol* 63:1651–1660 (1989)) by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

```
                                           (SEQ ID NO:20)
5'-CGAGGTTAAAAAACGTCTAGGCCCCCCGAACCACGGGGACGTGGTTT
   TaqI
TCCTTTGAAAAACACGATTGC-3'
                XhoI
```

This sequence matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

Example 3

Biological Activity of Expressed Aggrecanase

To measure the biological activity of the expressed aggrecanase-related proteins obtained in Example 2 above, the proteins are recovered from the cell culture and purified by isolating the aggrecanase-related proteins from other proteinaceous materials with which they are co-produced as well as from other contaminants. Purification is carried out using standard techniques known to those skilled in the art. The purified protein is assayed in accordance with the following assays:

Assays specifically to determine if the protein is an enzyme capable of cleaving aggrecan at the aggrecanase cleavage site:

1. Flourescent peptide assay: Expressed protein is incubated with a synthetic peptide which encompasses amino acids at the aggrecanase cleavage site of aggrecan. One side of the synthetic peptide has a flourophore and the other a quencher. Cleavage of the peptide separates the flourophore and quencher and elicits flourescence. From this assay it can be determined that the expressed protein can cleave aggrecan at the aggrecanase site, and relative flourescence tells the relative activity of the expressed protein.

2. Neoepitope western: Expressed protein is incubated with intact aggrecan. After several biochemical manipulations of the resulting sample (dialysis, chondroitinase treatment, lyophilization and reconstitution) the sample is run on an SDS PAGE gel. The gel is incubated with an antibody that only recognizes a site on aggrecan exposed after aggrecanase cleavage. The gel is transferred to nitrocellulose and developed with a secondary antibody to result in bands running at a molecular weight consistent with aggrecanase generated cleavage products of aggrecan. This assay, called a western assay, shows whether the expressed protein cleaved native aggrecan at the aggrecanase cleavage site, and also provides the molecular weight of the cleavage products. Relative density of the bands can give some idea of relative aggrecanase activity.

Assay to determine if an expressed protein can cleave aggrecan anywhere in the protein (not specific to the aggrecanase site):

3. Aggrecan ELISA: Expressed protein is incubated with intact aggrecan which had been previously adhered to plastic wells. The wells are washed and then incubated with an antibody that detects aggrecan. The wells are developed with a secondary antibody. If there is the original amount of aggrecan remaining in the well, the antibody will densely stain the well. If aggrecan was digested off the plate by the expressed protein, the antibody will demonstrate reduced staining due to reduced aggrecan concentration. This assay tells whether an expressed protein is capable of cleaving aggrecan (anywhere in the protein, not only at the aggrecanase site) and can determine relative aggrecan cleaving.

Protein analysis of the purified proteins is conducted using standard techniques such as SDS-PAGE acrylamide (Laemmli, Nature 227:680 (1970)) stained with silver (Oakley, et al., *Anal Biochem.* 105:361 (1980)) and by immunoblot (Towbin, et al., *Proc. Natl. Acad. Sci. USA* 76:4350 (1979)). Using the above described assays, expressed aggrecanase-related proteins are evaluated for their activity and useful aggrecanase-related molecules are identified.

Example 4

Preparation of Antibodies

An antibody against a novel aggrecanase molecule is prepared. To develop an antibody capable of inhibiting aggrecanase activity, a group of mice are immunized every two weeks with a novel aggrecanase protein mixed in Freunds complete adjuvant for the first two immunizations, and incomplete Freunds adjuvant thereafter. Throughout the immunization period, blood is sampled and tested for the presence of circulating antibodies. At week 9, an animal with circulating antibodies is selected, immunized for three consecutive days, and sacrificed. The spleen is removed and homogenized into cells. The spleen cells are fused to a myeloma fusion partner (line P3-x63-Ag8.653) using 50% PEG 1500 by an established procedure (Oi & Herzenberg, *Selected Methods in Cellular Immunology*, W. J. Freeman Co., San Francisco, Calif., at 351 (1980)). The fused cells are plated into 96-well microtiter plates at a density of $2\times10^5$ cells/well. After 24 hours, the cells are subjected to HAT selection (Littlefield, *Science*, 145: 709 (1964)) effectively killing any unfused and unproductively fused myeloma cells.

Successfully fused hybridoma cells secreting anti-aggrecanase antibodies are identified by solid and solution phase ELISAs. Novel aggrecanase protein is prepared from CHO cells as described above and coated on polystyrene (for solid phase assays) or biotinylated (for a solution based assay). Neutralizing assays are also employed where aggrecan is coated on a polystyrene plate and biotin aggrecanase activity is inhibited by the addition of hybridoma supernatant. Results identify hybridomas expressing aggrecanase antibodies. These positive clones are cultured and expanded for further study. These cultures remain stable when expanded and cell lines are cloned by limiting dilution and cryopreserved.

From these cell cultures, a panel of antibodies is developed that specifically recognize aggrecanase proteins. Isotype of the antibodies is determined using a mouse immunoglobulin isotyping kit (Zymed™ Laboratories, Inc., San Francisco, Calif.).

Example 5

Method of Detecting Level of Aggrecanase

The anti-aggrecanase antibody prepared according to Example 4 can be used to detect the level of aggrecanase in a sample The antibody can be used in an ELISA, for example, to identify the presence or absence, or quantify the amount of, aggrecanase in a sample. The antibody is labeled with a fluorescent tag. In general, the level of aggrecanase in a sample can be determined using any of the assays disclosed in Example 3.

Example 6

Method of Treating a Patient

The antibody developed according to Example 4 can be administered to patients suffering from a disease or disorder related to the loss of aggrecan, or excess aggrecanase activity. Patients take the composition one time or at intervals, such as once daily, and the symptoms and signs of their disease or disorder improve. For example, loss of aggrecan would decrease or cease and degradation of articular cartilage would decrease or cease. Symptoms of osteoarthritis would be reduced or eliminated. This shows that the composition of the invention is useful for the treatment of diseases or disorders related to the loss of aggrecan, or excess aggrecanase activity. The antibodies can also be used with patients susceptible to osteoarthritis, such as those who have a family history or markers of the disease, but have not yet begun to suffer its effects.

| Patient's Condition | Route of Administration | Dosage | Frequency | Predicted Results |
|---|---|---|---|---|
| Osteoarthritis | Subcutaneous | 500 µg/kg | Daily | Decrease in symptoms |
| " | " | 1 mg/kg | Weekly | Decrease in symptoms |

| Patient's Condition | Route of Administration | Dosage | Frequency | Predicted Results |
| --- | --- | --- | --- | --- |
| " | Intramuscular | 500 µg/kg | Daily | Decrease in symptoms |
| " | " | 1 mg/kg | Weekly | Decrease in symptoms |
| " | Intravenous | 500 µg/kg | Daily | Decrease in symptoms |
| " | " | 1 mg/kg | Weekly | Decrease in symptoms |
| Family History of Osteoarthritis | Subcutaneous | 500 µg/kg | Daily | Prevention of condition |
| Family History of Osteoarthritis | Intramuscular | 500 µg/kg | Daily | Prevention of condition |
| Family History of Osteoarthritis | Intravenous | 500 µg/kg | Daily | Prevention of condition |

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto. All of the documents cited in this application are incorporated by reference in their entirety. Additionally, all sequences cited in databases and all references disclosed are incorporated by reference in their entirety.

What is claimed is:

1. A purified aggrecanase protein comprising the amino acid sequence set forth in SEQ ID NO: 4.

2. A method for identifying inhibitors of aggrecanase comprising
   a) providing a purified aggrecanase protein comprising the amino acid sequence set forth in SEQ ID NO:4;
   b) assaying the aggrecanase activity of the aggrecanase protein in the presence of a potential inhibitor; and
   c) identifying an inhibitor of aggrecanase activity.

* * * * *